US008691986B2

(12) United States Patent
Allen et al.

(10) Patent No.: US 8,691,986 B2
(45) Date of Patent: Apr. 8, 2014

(54) AZETIDINE AND PIPERIDINE COMPOUNDS USEFUL AS PDE10 INHIBITORS

(71) Applicant: Amgen Inc., Thousand Oaks, CA (US)

(72) Inventors: Jennifer R. Allen, Newbury Park, CA (US); Jian J. Chen, Camarillo, CA (US); Michael J. Frohn, Thousand Oaks, CA (US); Matthew R. Kaller, Ventura, CA (US); Qingyian Liu, Camarillo, CA (US); Thomas T. Nguyen, Newbury Park, CA (US); Alexander J. Pickrell, Westlake Village, CA (US); Wenyuan Qian, Newbury Park, CA (US); Robert M. Rzasa, Ventura, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/917,699

(22) Filed: Jun. 14, 2013

(65) Prior Publication Data
US 2013/0338138 A1    Dec. 19, 2013

Related U.S. Application Data

(60) Provisional application No. 61/659,911, filed on Jun. 14, 2012.

(51) Int. Cl.
*C07D 241/00* (2006.01)
*C07D 239/70* (2006.01)
*C07D 471/02* (2006.01)
*C07D 215/00* (2006.01)

(52) U.S. Cl.
USPC ............ 544/336; 544/253; 546/122; 546/152

(58) Field of Classification Search
None
See application file for complete search history.

(56) References Cited

U.S. PATENT DOCUMENTS

2011/0306587 A1    12/2011    Allen et al.

FOREIGN PATENT DOCUMENTS

| EP | 0 039 051 A2 | 11/1981 |
| WO | WO 2011/143129 A1 | 11/2011 |
| WO | WO 2011/143365 A1 | 11/2011 |
| WO | WO 2011/143366 A1 | 11/2011 |
| WO | WO 2011/143495 A1 | 11/2011 |

OTHER PUBLICATIONS

Alavijeh, et al., "Drug Metabolism and Pharmacokinetics, the Blood-Brain Barrier, and Central Nervous System Drug Discovery," NeuroRx: the Journal of the American Society for Experimental NeuroTherapeutics, 2005, 2:554-571.
Bundgaard, et al., "A Novel Solution-Stable, Water-Soluble Prodrug Type for Drugs Containing a Hydroxyl or an NH-Acidic Group," Journal of Medicinal Chemistry, 1989, 32(12): 2503-2507.
Celen, et al., "Preclinical Evaluation of $^{18}$F-JNJ41510417 as a Radioligand for PET Imaging of Phosphodiesterase-10A in the Brain," Journal of Nuclear Medicine, 2010, 51(10):1584-1591.
Fujishige, et al., Cloning and Characterization of a Novel Human Phosphodiesterase That Hydrolyzes Both cAMP and cGMP (PDE10A), Journal of Biological Chemistry, 1999, 274(26):18438-18445.
Giedd, et al., "MRI Assessment of Children With Obsessive-Compulsive Disorder or Tics Associated With Streptococcal Infection," American Journal of Psychiatry, 2000, 157:281-283.
Loughney, et al., "Isolation and characterization of PDE10A, a novel human 3', 5'-cyclic nucleotide phyosphodiesterase," Gene, 1999, 234:109-117.
Obeso, et al., "The origin of motor fluctuations in Parkinson's disease: Importance of dopaminergic innervation and basal ganglia circuits," Neurology, 2004, 62(Suppl. 1): S17-S30.
Saxena, et al., "Neuroimaging and frontal-subcortical circuitry in obsessive-compulsive disorder," British Journal of Psychiatry, 1998, 173(Suppl. 35):26-37.
Soderling, et al., "Isolation and characterization of a dual-substrate phosphodiesterase gene family:PDE10A," Proc. Natl. Acad. Sci. USA, 1999, 96:7071-7076.
Svensson, et al., "The Design and Bioactivation of Presystemically Stable Prodrugs," Drug Metabolism Reviews, 1988, 19(2):165-194.
International Search Report for PCT/US2013/045768, Azetidine and Piperidine Compounds Useful as PDE10 Inhibitors, mail date Jul. 23, 2013.

*Primary Examiner* — James O Wilson
*Assistant Examiner* — Oluwafemi Masha
(74) *Attorney, Agent, or Firm* — Elsa D. Lemoine

(57) ABSTRACT

Azetidine and piperidine compounds of formula (I):

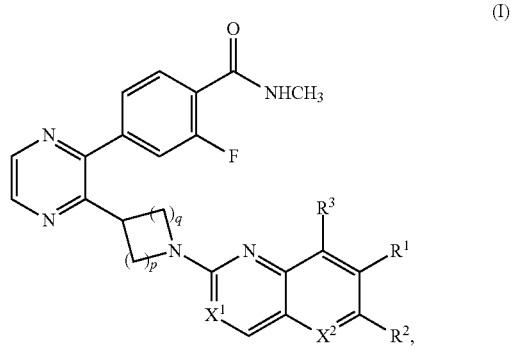

as defined in the specification, compositions containing them, and processes for preparing such compounds and intermediates thereof. Provided herein also are methods of treating cognitive disorders or diseases treatable by inhibition of PDE10, such as Huntington's Disease, schizophrenia, bipolar disorder, obsessive-compulsive disorder, and the like.

8 Claims, No Drawings

AZETIDINE AND PIPERIDINE COMPOUNDS USEFUL AS PDE10 INHIBITORS

CROSS REFERENCE TO RELATED APPLICATIONS

This application claims the benefit of U.S. Provisional Application No. 61/659,911, filed Jun. 14, 2012, which is hereby incorporated by reference.

FIELD OF THE INVENTION

Provided herein are novel azetidine and piperidine compounds that are PDE10 inhibitors, pharmaceutical compositions containing such compounds, and processes for preparing such compounds. Provided herein also are methods of treating cognitive disorders or diseases treatable by inhibition of PDE10, such as Huntington's Disease, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kilobases, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds of the invention can be labeled with either positron or gamma emitting radionuclides. For imaging, the most commonly used positron emitting (PET) radionuclides are $^{11}C$, $^{18}F$, $^{15}O$, $^{13}N$, $^{76}Br$, $^{77}Br$, $^{123}I$, or $^{125}I$, wherein $^{11}C$, $^{18}F$, $^{123}I$, or $^{125}I$ are preferred, all of which are accelerator produced. In the two decades, one of the most active areas of nuclear medicine research has been the development of receptor imaging radiotracers. These tracers bind with high affinity and specificity to selective receptors and neuroreceptors. For example, Johnson and Johnson has synthesized and evaluated $^{18}F$-JNJ41510417 as a selective and high-affinity radioligand for in vivo brain imaging of PDE10A using PET (The Journal Of Nuclear Medicine; Vol. 51; No. 10; October 2010).

The present inventors have made an extensive study for the purpose of developing compounds for treating cognitive disorder, preferably schizophrenia, which would be not only effective for improving the negative symptoms, but also effective for improving the positive symptoms of schizophrenia, furthermore such compounds would have less side-effects as compared with those shown by drugs known in prior art. As the result, the present inventors have successfully found novel azetidine and piperidine compounds having strong and selective inhibition activity against PDE10 receptors. Alternatively, it is also preferable that the novel azetidine and piperidine compounds can be developed for treating Huntington's Disease.

Azetidine and piperidine compounds disclosed in WO2011/143365 have substituents different from those of the azetidine and piperidine compounds of the present invention.

Neuroscience is a particularly challenging field in drug development. Complexities in molecular signaling and electrical circuitry make it difficult to understand disease and design treatment and the blood-brain barrier stands in the way of therapies. The brain is arguably our most vital organ, and is extremely sensitive to chemicals in its environment. The blood-brain barrier (BBB) protects the brain from damage by keeping many foreign and natural molecules from entering. It surrounds all blood vessels that feed the brain. It is composed of a single layer of cells, tightly bound together. It is not sufficient for a potential neurotherapeutic agent to move across the BBB, it also has to stay in the brain long enough to exert its desired action. This means that it also has to avoid being a substrate for a variety of transport proteins that work to extrude compounds from the brain. There are at least six such outwardly directed active efflux mechanisms in the BBB (Alavijeh et al. NeuroRx. 2005 October; 2(4): 554-571, see p. 565, FIG. 3), the most prominent of which is a phosphorylated glycoprotein called P-glycoprotein (P-gp), a 170-kDa member of the ATP-binding cassette (ABC) superfamily of membrane transporters, which in humans is encoded by multidrug resistance gene 1 (MDR1). P-gp is located on the apical surface of the endothelial cells of the brain capillaries toward the vascular lumen and contributes to the poor BBB penetration of a number of drugs. In a study of the concentration of 32 structurally diverse CNS drugs in brain, plasma, and CSF of wild-type and (P-gp) knockout mice, 29 of these drugs showed marked differences in brain/plasma ratios between knockout and wild-type mice. There have been attempts to establish quantitative structure-activity relationship (QSAR) for P-gp, but the task is made difficult by the broad specificity of this transporter.

Under these circumstances, development of drugs for treating cognitive disorders, such as schizophrenia, having improved Central Nervous System (CNS) drug profile such as high permeability, low efflux, high receptor or target occupancy, and high PDE10 selectivity profile have been eagerly needed.

SUMMARY OF THE INVENTION

The present invention comprises a novel azetidine and piperidine compounds having improved CNS drug profile useful in the treatment of cognitive diseases, such as PDE10-mediated diseases and other maladies, such as schizophrenia, Huntington's Disease, bipolar disorder, or obsessive-compulsive disorder. Accordingly, the invention also comprises pharmaceutical compositions comprising the compounds, methods for the treatment of PDE10-mediated cognitive diseases and other maladies, such as schizophrenia, Huntington's Disease, bipolar disorder, or obsessive-compulsive disorder, using the compounds and compositions of the invention, and intermediates and processes useful for the preparation of the compounds of the invention.

Another aspect of the invention comprises novel azetidine and piperidine compounds radiolabeled with a positron emitting radionuclide selected from $^{11}C$, $^{18}F$, $^{15}O$, $^{13}N$, $^{76}Br$, $^{77}Br$, $^{123}I$, or $^{125}I$, a radiopharmaceutical composition comprising the radiolabelled compound, a method for the diagnostic imaging of PDE10 receptors in a mammal, including human, or tissues bearing PDE10 receptors in a mammal, including human brain, which comprises administering to a mammal in need of such diagnostic imaging an effective amount of the radiolabeled compound, and a method for the detection or quantification of PDE10 enzyme in mammalian tissue, including human tissue, which comprises contacting such mammalian tissue in which such detection or quantification is desired with an effective amount of the radiolabeled compound.

The compounds of the invention are represented by the following general structure:

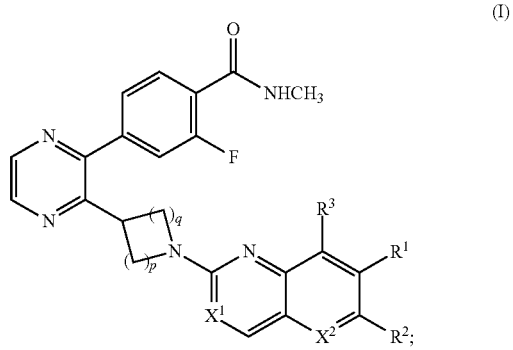
(I)

or a pharmaceutically acceptable salt thereof, wherein p, q, $R^1$, $R^2$, $R^3$, $X^1$ and $X^2$ are defined below.

DETAILED DESCRIPTION OF THE INVENTION

One aspect of the current invention relates to compounds having the general structure of formula (I):

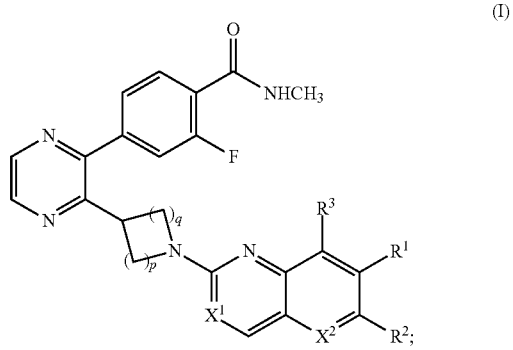
(I)

or a pharmaceutically acceptable salt thereof, wherein:
$X^1$ is N or $CR^4$;
$X^2$ is N or $CR^5$;
wherein 0 to 1 of $X^1$ and $X^2$ are N;
each of p and q is independently 1 or 2; wherein the sum of p and q is 2 or 4;
and each $R^1$, $R^2$, $R^3$, $R^4$, and $R^5$ is independently hydrogen or halo.

In one embodiment, $X^1$ is N and $X^2$ is CH.
In another embodiment, $X^1$ is CH and $X^2$ is N.
In another embodiment, $X^1$ is CH and $X^2$ is CH.
In another embodiment, the sum of p and q is 4.
In another embodiment, the sum of p and q is 2.
In another embodiment, s$R^2$ is fluoro.
In another embodiment, one of $R^1$, $R^2$, and $R^3$ is hydrogen.
In another embodiment, two of $R^1$, $R^2$, and $R^3$ are hydrogen.
In another embodiment, $R^1$, $R^2$, and $R^3$ are hydrogen.
In another embodiment, one of $R^1$ and $R^2$ is fluoro.
In another embodiment, one of $R^1$ and $R^2$ is chloro.
In another embodiment, $R^1$ is chloro and $R^2$ is fluoro.
In another embodiment, $R^1$ is fluoro or chloro.
In another embodiment, $R^1$ is hydrogen and $R^2$ is chloro or fluoro.
In another embodiment, $R^1$ is chloro or fluoro and $R^2$ is hydrogen.

Another aspect of the invention relates to a compound, or a pharmaceutically acceptable salt thereof, which is tabulated below: (Ex. No. is Example No.)

| Ex. No. | Structure | Name |
|---|---|---|
| 1 | 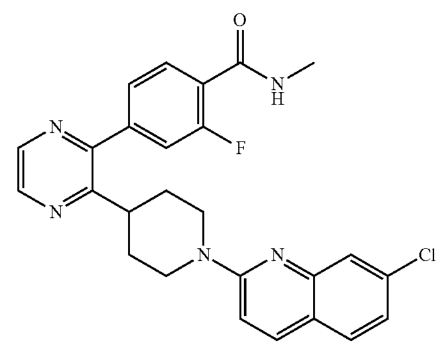 [SMILES: CNC(=O)c1ccc(-c2nccnc2C2CCN(c3ccc4ccc(Cl)cc4n3)CC2)cc1F] | 4-(3-(1-(7-chloro-2-quinolinyl)-4-piperidinyl)-2-pyrazinyl)-2-fluoro-N-methylbenzamide |
| 2 | 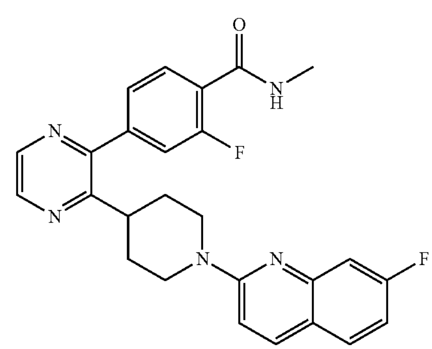 [SMILES: CNC(=O)c1ccc(-c2nccnc2C2CCN(c3ccc4ccc(F)cc4n3)CC2)cc1F] | 2-fluoro-4-(3-(1-(7-fluoroquinolin-2-yl)piperidin-4-yl)pyrazin-2-yl)-N-methylbenzamide |
| 3 | 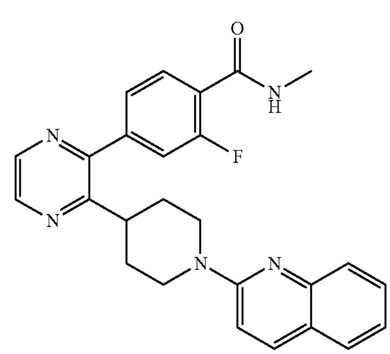 [SMILES: CNC(=O)c1ccc(-c2nccnc2C2CCN(c3ccc4ccccc4n3)CC2)cc1F] | 2-fluoro-N-methyl-4-(3-(1-(2-quinolinyl)-4-piperidinyl)-2-pyrazinyl)benzamide |

-continued
| 4 | 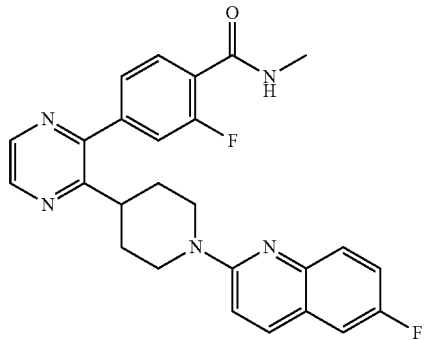 [SMILES: CNC(=O)c1ccc(-c2nccnc2C2CCN(c3ccc4cc(F)ccc4n3)CC2)cc1F] | 2-fluoro-4-(3-(1-(6-fluoro-2-quinolinyl)-4-piperidinyl)-2-pyrazinyl)-N-methylbenzamide |
| 5 | 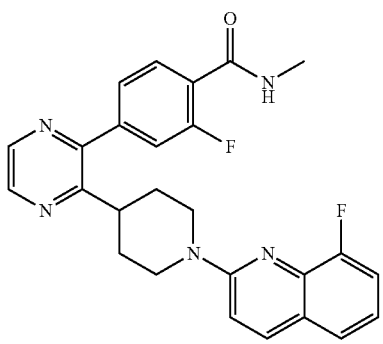 [SMILES: CNC(=O)c1ccc(-c2nccnc2C2CCN(c3ccc4cccc(F)c4n3)CC2)cc1F] | 2-fluoro-4-(3-(1-(8-fluoro-2-quinolinyl)-4-piperidinyl)-2-pyrazinyl)-N-methylbenzamide |
| 6 | 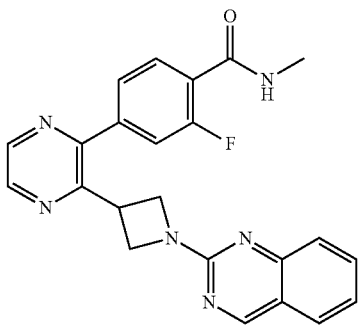 [SMILES: CNC(=O)c1ccc(-c2nccnc2C2CN(c3ncc4ccccc4n3)C2)cc1F] | 2-fluoro-N-methyl-4-(3-(1-(2-quinazolinyl)-3-azetidinyl)-2-pyrazinyl)benzamide |
| 7 | 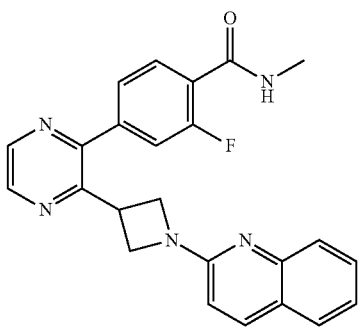 [SMILES: CNC(=O)c1ccc(-c2nccnc2C2CN(c3ccc4ccccc4n3)C2)cc1F] | 2-fluoro-N-methyl-4-(3-(1-(2-quinolinyl)-3-azetidinyl)-2-pyrazinyl)benzamide |

-continued

| | | |
|---|---|---|
| 8 | 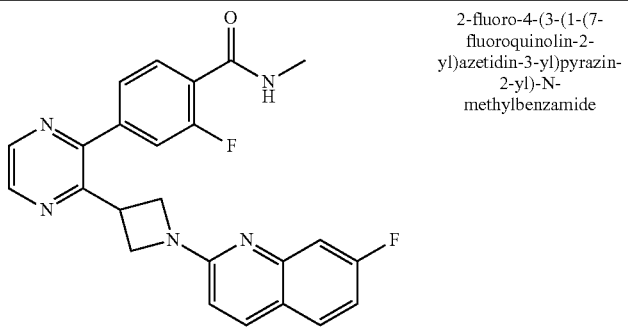 | 2-fluoro-4-(3-(1-(7-fluoroquinolin-2-yl)azetidin-3-yl)pyrazin-2-yl)-N-methylbenzamide |
| 9 | 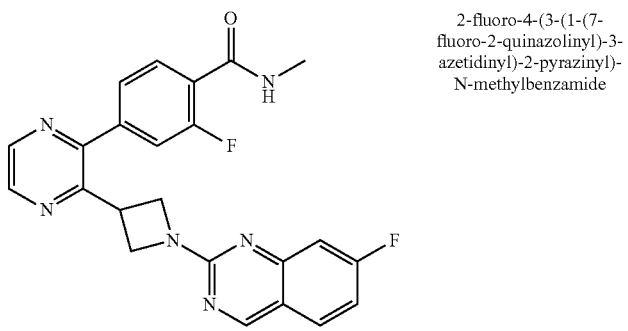 | 2-fluoro-4-(3-(1-(7-fluoro-2-quinazolinyl)-3-azetidinyl)-2-pyrazinyl)-N-methylbenzamide |
| 10 | 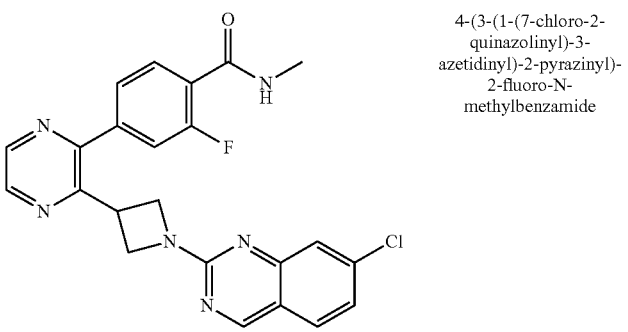 | 4-(3-(1-(7-chloro-2-quinazolinyl)-3-azetidinyl)-2-pyrazinyl)-2-fluoro-N-methylbenzamide |
| 11 | 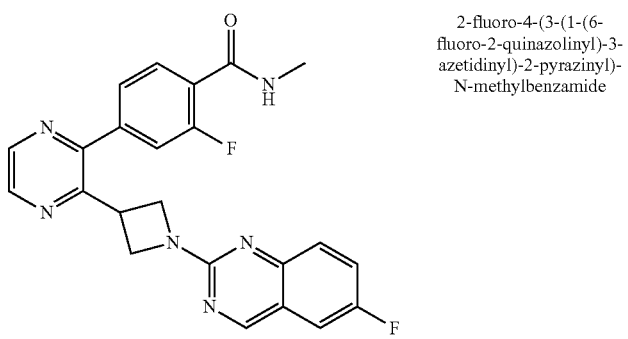 | 2-fluoro-4-(3-(1-(6-fluoro-2-quinazolinyl)-3-azetidinyl)-2-pyrazinyl)-N-methylbenzamide |
| 12 | 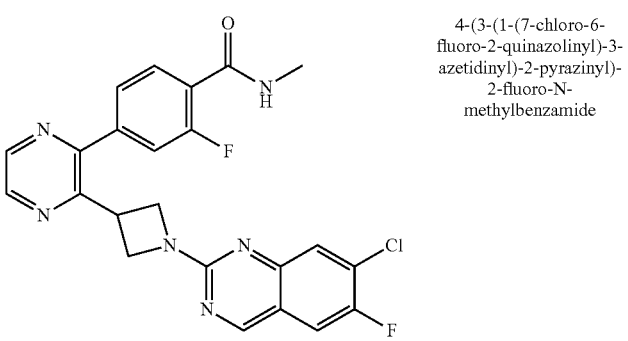 | 4-(3-(1-(7-chloro-6-fluoro-2-quinazolinyl)-3-azetidinyl)-2-pyrazinyl)-2-fluoro-N-methylbenzamide |

| | | |
|---|---|---|
| 13 | 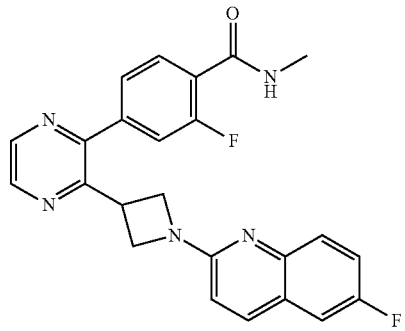 [SMILES: CNC(=O)c1ccc(-c2nccnc2C2CN(c3ccc4cc(F)ccc4n3)C2)cc1F] | 2-fluoro-4-(3-(1-(6-fluoro-2-quinolinyl)-3-azetidinyl)-2-pyrazinyl)-N-methylbenzamide |
| 14 | 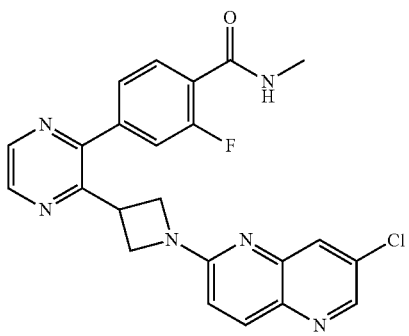 [SMILES: CNC(=O)c1ccc(-c2nccnc2C2CN(c3ccc4ncc(Cl)cc4n3)C2)cc1F] | 4-(3-(1-(7-chloro-1,5-naphthyridin-2-yl)-3-azetidinyl)-2-pyrazinyl)-2-fluoro-N-methylbenzamide |

Another aspect of the invention relates to a pharmaceutical composition comprising any one of the above compounds, or a pharmaceutically acceptable salt thereof, and a pharmaceutically-acceptable excipient.

Another aspect of the invention relates to a method of treating cognitive disorder or conditions that may be treated with PDE10 inhibitors comprising the step of administering to a patient in need thereof a therapeutically effective amount of any one of the above compounds, or a pharmaceutically acceptable salt thereof.

In one embodiment of the method, said conditions is psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, or compulsions with pallidal disease.

In another embodiment of the method, said condition is schizophrenia, Huntington's Disease, bipolar disorder, or obsessive-compulsive disorder.

In another embodiment of the method, said condition is schizophrenia.

Another aspect of the invention relates to the use of any one of the above compounds, or a pharmaceutically acceptable salt thereof, as a medicament.

Another aspect of the invention relates to the use of any one of the above compounds, or a pharmaceutically acceptable salt thereof in the manufacture of a medicament for the treatment of schizophrenia, Huntington's Disease, bipolar disorder, or obsessive-compulsive disorder.

Another aspect of the invention relates to a method of preparing a compound Formula (I), as defined above; comprising the step of:

(a) reacting a compound of formula 3 with a compound of formula 5:

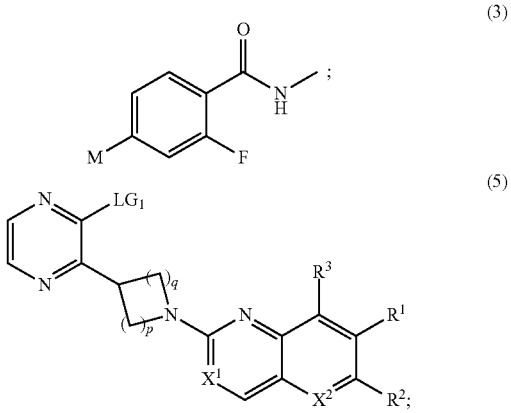

wherein $X^1$, $X^2$, $R^1$, $R^2$, $R^3$, p and q are as defined in the compound of formula (I); and wherein $LG_1$ is a leaving group and M is a metal moeity; in the presence of a solvent and a catalyst; or (b) reacting a compound of formula 2 with a compound of formula 4:

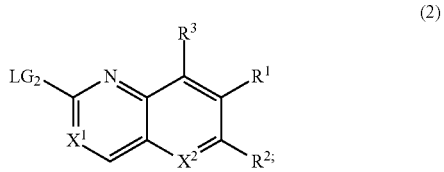

-continued

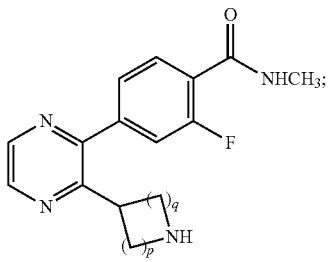
(4)

wherein $X^1$, $X^2$, $R^1$, $R^2$, $R^3$, p and q are as defined in the compound of formula (I), and $LG_2$ is a leaving group; in the presence of a solvent and a base; to prepare the compound of formula (I).

Another aspect of the invention relates to a compound, or a pharmaceutically acceptable salt thereof, of formula:

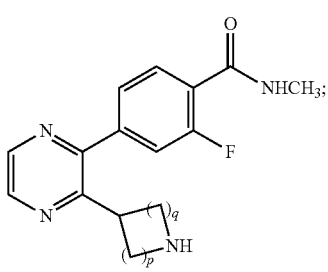
(4)

wherein each of p and q is independently 1 or 2; and wherein the sum of p and q is 2 or 4. In one embodiment, the sum of p and q is 4. In another embodiment, the sum of p and q is 2.

Another aspect of the invention relates to a compound, or a pharmaceutically acceptable salt thereof, of formula:

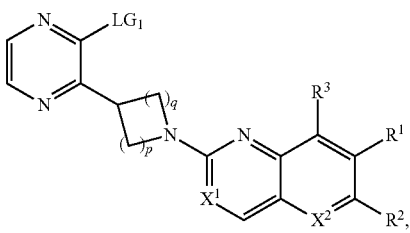
(5)

wherein
$X^1$ is N or $CR^4$;
$X^2$ is N or $CR^5$;
wherein 0 to 1 of $X^1$ and $X^2$ are N;
each of p and q is independently 1 or 2; wherein the sum of p and q is 2 or 4;
each $R^1$, $R^2$, $R^3$, $R^4$, and $R^5$ is independently hydrogen or halo; and $LG_1$ is a leaving group, such as halo.

In one embodiment of compound of formula (5), the sum of p and q is 4.

In another embodiment of compound of formula (5), the sum of p and q is 2.

Yet another aspect of the current invention relates to any compound of the present invention, or a pharmaceutically-acceptable salt thereof, radiolabeled with a positron emitting radionuclide selected from $^{11}C$, $^{18}F$, $^{15}O$, $^{13}N$, $^{76}Br$, $^{77}Br$, $^{123}I$ or $^{125}I$.

Yet another aspect of the current invention relates to a radiopharmaceutical composition comprising any compound of the present invention, or a pharmaceutically-acceptable salt thereof, radiolabeled with a positron emitting radionuclide selected from $^{11}C$, $^{18}F$, $^{15}O$, $^{13}N$, $^{76}Br$, $^{77}Br$, $^{123}I$, or $^{125}I$, and at least one pharmaceutically acceptable carrier or excipient.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of any compound of the present invention, or a pharmaceutically-acceptable salt thereof, radiolabeled with a positron emitting radionuclide selected from $^{11}C$, $^{18}F$, $^{15}O$, $^{13}N$, $^{76}Br$, $^{77}Br$, $^{123}I$, or $^{125}I$.

Yet another aspect of the current invention relates to a method for the detection or quantification of PDE10 receptors in mammalian tissue, including human tissue, which comprises contacting such mammalian tissue in which such detection or quantification is desired with an effective amount of any compound of the present invention, or a pharmaceutically-acceptable salt thereof, radiolabeled with a positron emitting radionuclide selected from $^{11}C$, $^{18}F$, $^{15}O$, $^{13}N$, $^{76}Br$, $^{77}Br$, $^{123}I$, or $^{125}I$.

Yet another aspect of the invention relates to PET tracers such as the present radiolabeled PDE 10 inhibitors and currently available PET technology can be used, but is not limited to, to obtain the following information: relationship between level of receptor or target occupancy by candidate PDE 10 inhibitors and clinical efficacy in patients; dose selection for clinical trials of PDE10 inhibitors prior to initiation of long term clinical studies; comparative potencies of structurally novel PDE10 inhibitors; investigating the influence of PDE10 inhibitors on in vivo transporter affinity and density during the treatment of clinical targets with PDE10 inhibitors and other agents; changes in the density and distribution of PDE10, for example, 1) during the active stage of a psychiatric disease or condition, 2) for the evaluation of efficacy during treatment, or 3) during remission; changes in PDE10 expression and distribution in CNS disorders; imaging neurodegenerative disease when PDE10 is upregulated; imaging neurodegenerative disease when PDE10 is involved; and the like.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor or target occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

The term "$C_{\alpha-\beta}$alkyl" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alkyl indicates a direct bond. Examples of $C_{1-6}$alkyl include, but are not limited to the following:

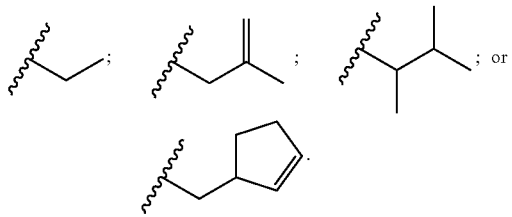

The term "halo" or "halogen" means a halogen atoms selected from F, Cl, Br or I.

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For additional examples of "pharmacologically acceptable salts," and Berge et al., J. Pharm. Sci. 66:1 (1977).

The term "substituted" means that a hydrogen atom on a molecule or group is replaced with a group or atom. Typical substitutents include: halogen, $C_{1-8}$alkyl, hydroxyl, $C_{1-8}$alkoxy, $-NR^xR^x$, nitro, cyano, halo or perhalo$C_{1-8}$alkyl, $C_{2-8}$alkenyl, $C_{2-8}$alkynyl, $-SR^x$, $-S(=O)_2R^x$, $-C(=O)OR^x$, $-C(=O)R^x$, wherein each $R^x$ is independently hydrogen or $C_1$-$C_8$ alkyl. It is noted that when the substituent is $-NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile, or by metallic agent such as boronic acids or boronates under transition metal catalyzed coupling conditions. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene) benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

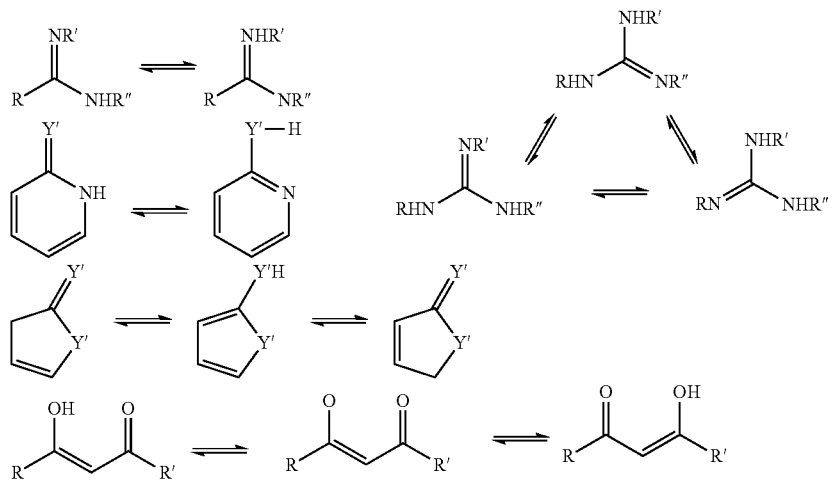

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

Utility and Methods of Use

Provided herein are methods for treating a cognitive disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the cognitive disorder or disease.

In certain embodiments, this invention provides a use of a compound as described herein in the manufacture of a medicament for treating a cognitive disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's Disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's Disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's Disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's Disease has been linked to a mutation of the protein huntingtin. In individuals who do not have Huntington's Disease, the protein huntingtin has a polyglutamine region containing about 8 to 31 glutamine residues. For individuals who have Huntington's Disease, the protein huntingtin has a polyglutamine region with over 37 glutamine residues. Aside from Huntington's Disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

Testing

The PDE10 inhibitory activities of the compounds of the present invention can be tested, for example, using the in vitro and in vivo and ex vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's Disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

Unless otherwise noted, all materials were purchased from Sinopharm Chemical Reagent Co., Ltd and used without further purification. All microwave assisted reactions were conducted with an Initiator® Synthesizer from Biotage®. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

GENERAL SCHEMES

The present invention further comprises procedures for the preparation of compounds of Formula (I). The compounds of Formula (I) can be synthesized according to the procedures described in the following Schemes A or B, wherein p, q, $R^1$, $R^2$, $R^3$, $X^1$ and $X^2$ are defined herein, except where further noted. The synthetic methods described below are merely exemplary, and the compounds of the invention may also be synthesized by alternate routes as appreciated by persons of ordinary skill in the art.

GENERAL SCHEME A:

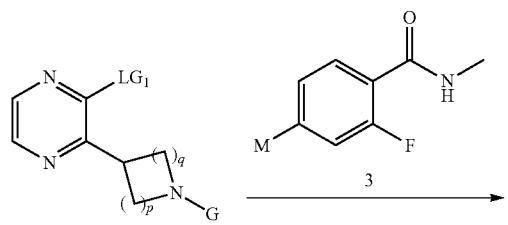

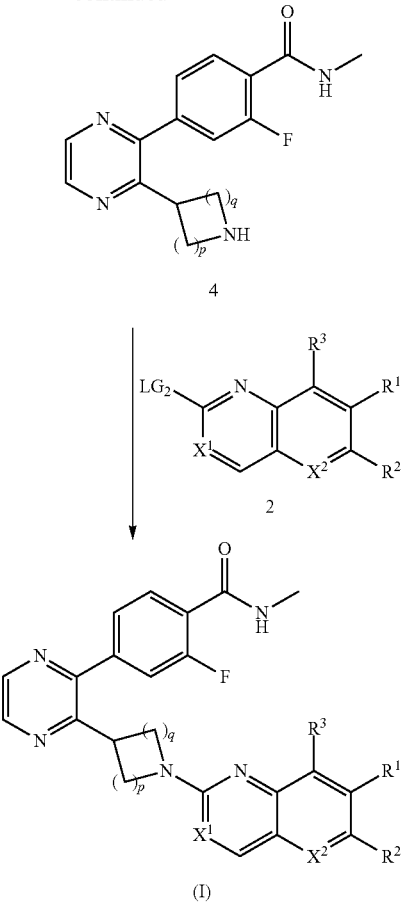

Preparation of Compound 2:

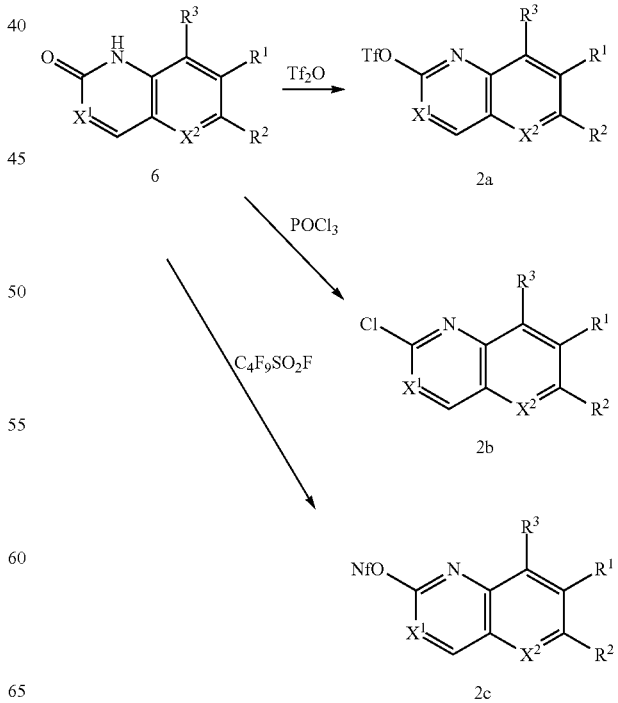

Preparation of Compound 1A:

Compound of formula 1a; wherein 1a G is an amino protecting group, such as tert-Butyloxycarbonyl (Boc), can prepared according to process described in WO 2011/143365; which can be followed by reacting with a deprotecting agent to afford compound of formula 1a; wherein G is H according to deprotection method known in the art.

A compound of formula (I) may be prepared by the method generally described in General Scheme A. As shown, a compound of formula (I) may be prepared by reacting a compound of formula 2, wherein $LG_2$ is a leaving group, such as triflate ($CF_3SO_3$ or OTf), halo (such as chloro), or nonafluorobutanesulfonate, with a compound of formula 4 in the presence of a solvent, such as dimethyl sulfoxide (DMSO), N,N-dimethylformamide (DMF), or acetonitrile, in the presence of a base, such as diisopropylethyl amine (DIPEA), triethyl amine (TEA), or potassium carbonate ($K_2CO_3$), at room temperature or up to 120° C. Compound of formula 4 can be prepared by reacting a compound of formula 1a, wherein $LG_1$ is a leaving group, such as halo, preferably chloro, and G is hydrogen or an amino protecting group, such as tert-Butyloxycarbonyl (Boc) or Carbobenzyloxy (Cbz), with a compound of formula 3 wherein M is boronic acid moiety or boronic ester moiety of formula —$B(OH)_2$ or —$B(OR)_2$ (wherein R is ($C_1$-$C_4$)alkyl)), Zn halide, or the like, in the presence of a catalyst under a coupling reaction condition, such as Suzuki reaction or Negeshi reaction. If G is an amino protecting group in the compound of formula 1a, the coupling reaction is followed by a deprotecting step by reacting a protected compound 4 with an amino deprotecting agent, such as concentrated, strong acid, such as HCl or $CF_3COOH$, or hydrogenolysis, to afford the compound of formula 4.

Preparation of Compound 2:

The compound of formula 2 that are not commercially available can be made according to General Scheme A by reacting a compound of formula 6 with an appropriate reagent and condition to afford a suitable leaving group $LG_2$. For example, a compound of formula 2a, wherein $LG_2$ is triflate ($CF_3SO_3$ or OTf) can be made by reacting a compound of formula 6 with trifluoromethanesulfonic anhydride ($Tf_2O$). Alternatively, a compound of formula 2b, wherein $LG_2$ is halo (such as chloro) can be made by reacting a compound of formula 6 with Phosphorus(V) oxychloride ($POCl_3$). Alternatively, a compound of formula 2c, wherein $LG_2$ is nonafluorobutanesulfonate, can be made by reacting a compound of formula 6 with 1-butanesulfonylfluoride ($C_4F_9SO_2F$). Compound 6 is commercially available or can be readily prepared according to the methods described herein.

Preparation of Compound 3:

The compound of formula 3 wherein M is —$B(OH)_2$ is commercially available. It can also be made according to General Scheme A by reacting the corresponding commercially available chloro- or bromo precursor compound with an appropriate catalyst and metalation agent and under appropriate condition to afford a suitable metal (M) moiety. For example, a compound of formula 3, wherein M is —$B(OH)_2$, can be made by reacting the corresponding bromo-precursor compound with $PdCl_2(PPh)_3$ catalyst in the presence of Bis (pinacolato)diboron ($C_{12}H_{24}B_2O_4$) and potassium acetate in non polar solvent, such as dioxane, at elevated temperature followed by conversion of the resulting pinacol boronate to the corresponding boronic acid.

GENERAL SCHEME B:
Alternative synthesis to compound of formula (I)

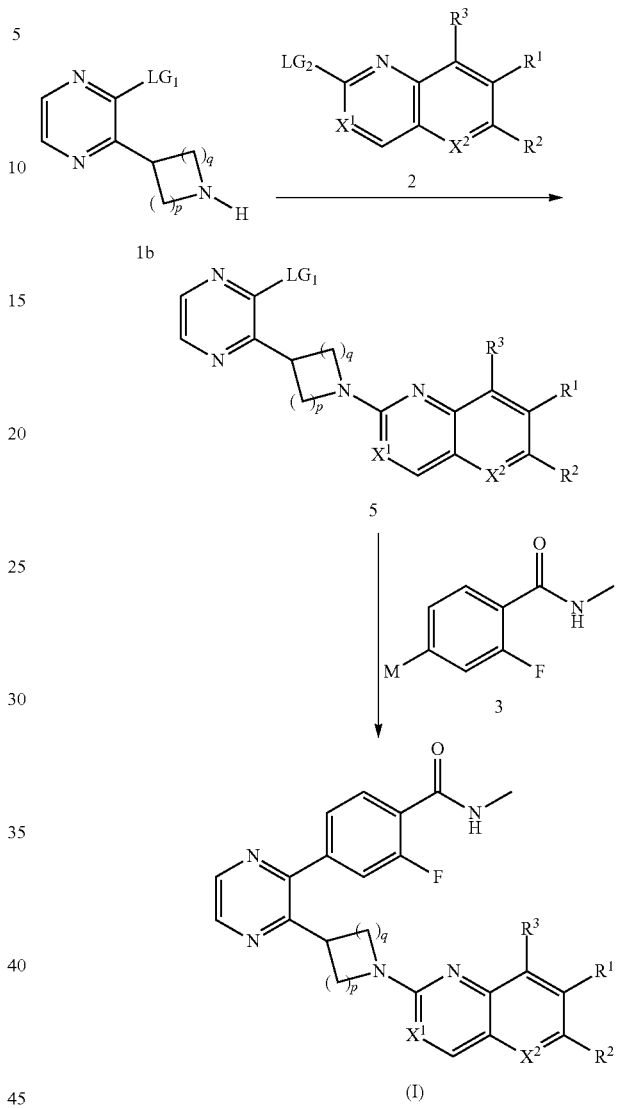

Alternatively a compound of formula (I) may be made by the method generally described in General Scheme B. As shown, a compound of formula (I) may be made by reacting a compound of formula 5, wherein $LG_1$ is a leaving group, such as triflate ($CF_3SO_3$ or OTf) or halo (such as chloro) with a compound of formula 3, wherein M is boronic acid moiety or boronic ester moiety of formula —$B(OH)_2$ or —$B(OR)_2$ (wherein R is ($C_1$-$C_4$)alkyl)), Zn halide, or the like, in the presence of a catalyst under a coupling reaction condition, such as Suzuki reaction or Negeshi reaction. Compound of formula 5 can be made by reacting a compound of formula 1b, wherein $LG_1$ is a leaving group, such as triflate ($CF_3SO_3$ or OTf) or halo (such as chloro), with a compound of formula 2 wherein $LG_2$ is a leaving group, such as triflate ($CF_3SO_3$ or OTf), halo (such as chloro), or nonafluorobutanesulfonate, in the presence of a solvent, such as DMSO, DMF, or acetonitrile, in the presence of a base, such as DIPEA, TEA, or $K_2CO_3$, at room temperature or up to 120° C.

Compounds of Formulas 1b, 2, 3 can be prepared according to General Scheme A.

SYNTHETIC EXAMPLES

The following list of abbreviations used or commonly used throughout the specification represent the following and should assist in understanding the invention:
ACN, MeCN acetonitrile
Aq., aq. aqueous
Ar argon (gas)
BOP benzotriazol-1-yl-oxy Hexafluorophosphate
BuLi Butyllithium
$Cs_2CO_3$ cesium carbonate
$CHCl_3$ chloroform
$CH_2Cl_2$, DCM dichloromethane, methylene chloride
Cu(1)I copper(1) iodide
DCC dicyclohexylcarbodiimide
DIC 1,3-diisopropylcarbodiimide
DIEA, DIPEA diisopropylethylamine
DME dimethoxyethane
DMF dimethylformamide
DMAP 4-dimethylaminopyridine
DMS dimethylsulfide
DMSO dimethylsulfoxide
EDC, EDCI 1-(3-dimethylaminopropyl)-3-ethylcarbodiimide
$Et_2O$ diethyl ether
EtOAc ethyl acetate
FBS fetal bovine serum
G, gm gram
h, hr hour
$H_2$ hydrogen
$H_2O$ water
HCl hydrochloric acid
HOAc acetic acid
HPLC high pressure liquid chromatography
IPA, IpOH isopropyl alcohol
$K_2CO_3$ potassium carbonate
KI potassium iodide
LG leaving group
LDA Lithium diisopropylamide
LiOH lithium hydroxide
$MgSO_4$ magnesium sulfate
MS or m/z mass spectrum
MeOH methanol
$N_2$ nitrogen
$NaCNBH_3$ sodium cyanoborohydride
$Na_2CO_3$ sodium carbonate
$NaHCO_3$ sodium bicarbonate
NaH sodium hydride
NaI sodium iodide
$NaBH_4$ sodium borohydride
NaOH sodium hydroxide
$Na_2SO_4$ sodium sulfate
$NH_4Cl$ ammonium chloride
$NH_4OH$ ammonium hydroxide
$P(t-bu)_3$ tri(tert-butyl)phosphine
PBS phosphate buffered saline
Pd/C palladium on carbon
$Pd(PPh_3)_4$ palladium(0)triphenylphosphine tetrakis
$Pd(dppf)Cl_2$ palladium(1,1-bisdiphenylphosphinoferrocene)(II)chloride
$Pd(PhCN)_2Cl_2$ palladium di-cyanophenyl dichloride
$Pd(OAc)_2$ palladium acetate
$Pd_2(dba)_3$ tris(dibenzylideneacetone) dipalladium
RT, rt room temperature
RBF, rbf round bottom flask
TLC, tlc thin layer chromatography
TEA, $Et_3N$ triethylamine
TFA trifluoroacetic acid
THF tetrahydrofuran The following preparations of compounds of Formula (I) and intermediates (References) are given to enable those skilled in the art to more clearly understand and to practice the present invention. They should not be considered as limiting the scope of the invention, but merely as being illustrative and representative thereof.

Example 1

4-(3-(1-(7-Chloroquinolin-2-Yl)Piperidin-4-Yl) Pyrazin-2-Yl)-2-Fluoro-N-Methylbenzamide

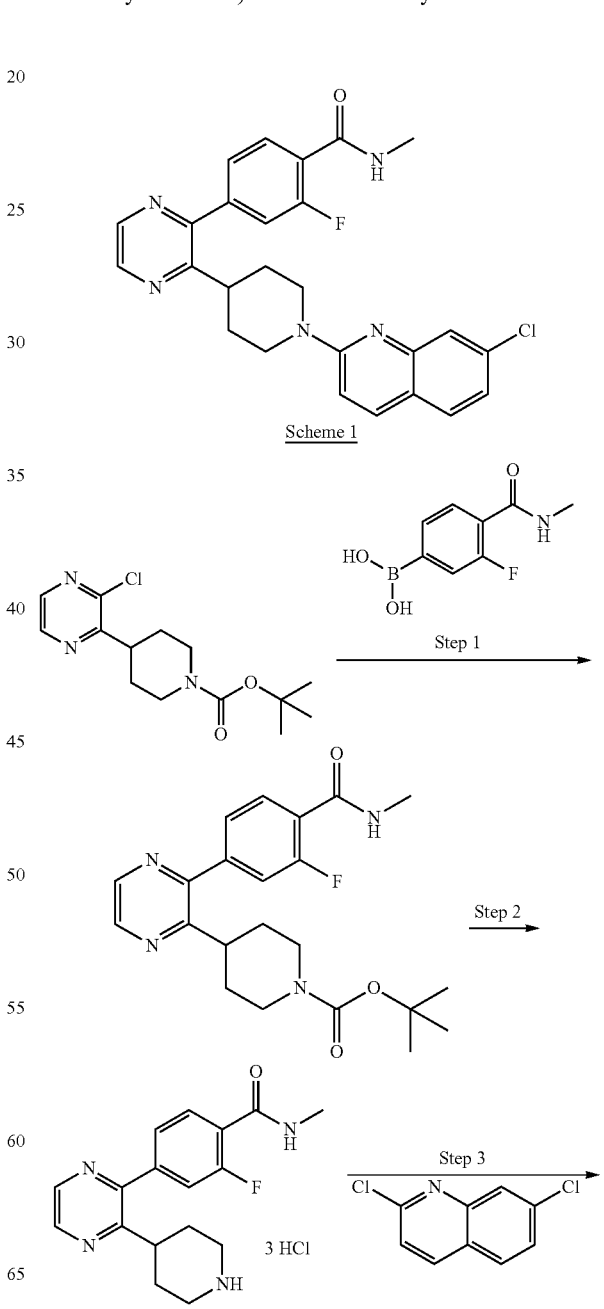

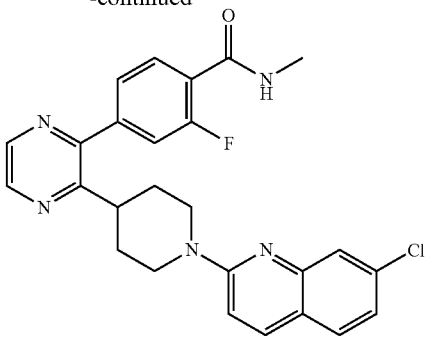

Step 1: Tert-Butyl 4-(3-(3-Fluoro-4-(Methylcarbamoyl)Phenyl) Pyrazin-2-Yl)Piperidine-1-Carboxylate To a round bottomed flask (RBF) was added tert-butyl 4-(3-chloropyrazin-2-yl)piperidine-1-carboxylate (2 g, 6.72 mmol), (3-fluoro-4-(methylcarbamoyl)phenyl)boronic acid (1.64 g, 8.33 mmol; Combi-Blocks), potassium phosphate (3.56 g, 16.79 mmol), Bis(di-tert-butyl(4-dimethylaminophenyl)phosphine)dichloropalladium(II) (0.476 g, 0.672 mmol), and dioxane (20 mL):Water (2 mL). The mixture was stirred at 90° C. After 16 h, the reaction was allowed to cool to room temperature and poured into water (50 mL). The aqueous solution was extracted with ethyl acetate (EtOAc) (3×25 mL). The combined EtOAc layers were concentrated in vacuo and adsorbed onto a plug of silica gel and chromatographed through a Redi-Sep® pre-packed silica gel column (40 g), eluting with 30-100% EtOAc in hexane, to provide tert-butyl 4-(3-(3-fluoro-4-(methylcarbamoyl)phenyl)pyrazin-2-yl)piperidine-1-carboxylate (2.46 g, 5.94 mmol, 88% yield), as a yellow solid.

Step 2: 2-Fluoro-N-Methyl-4-(3-(Piperidin-4-Yl)Pyrazin-2-Yl)Benzamide Trihydrochloride To a RBF was added tert-butyl 4-(3-(3-fluoro-4-(methylcarbamoyl)phenyl)pyrazin-2-yl)piperidine-1-carboxylate (2.40 g, 5.79 mmol) and methanol (20 mL) was added 4M HCl in dioxane (5 mL, 20.00 mmol). The solution was stirred at room temperature. After 96 h, the reaction was concentrated in vacuo to give 2-fluoro-N-methyl-4-(3-(piperidin-4-yl)pyrazin-2-yl)benzamide trihydrochloride (2.46 g, 5.81 mmol, 100% yield), as a yellow foam. The 3 HCl equivalent was determined from the weight of the compound, without further characterization.

Step 3: 4-(3-(1-(7-Chloroquinolin-2-Yl)Piperidin-4-Yl)Pyrazin-2-Yl)-2-Fluoro-N-Methylbenzamide To a mixture of 2-fluoro-N-methyl-4-(3-(piperidin-4-yl)pyrazin-2-yl)benzamide trihydrochloride (315 mg, 0.743 mmol), 2,7-dichloroquinoline (192 mg, 0.969 mmol), cesium carbonate (1211 mg, 3.72 mmol), dioxane (4 mL), and bis(tri-t-butylphosphine)palladium(0) (89 mg, 0.174 mmol). The solution was stirred at 90° C. After stirring for 5 h, the reaction was allowed to cool to room temperature and filtered. The solids were washed with EtOAc. The filtrate was concentrated to ½ it's orginal volume and purified by reverse-phase preparative HPLC (Shimadzu) on a Phenomenex Gemini column (10 micron, C18, 110 Å, Axia, 100×50 mm) eluting at 90 mL/min with a linear gradient of 10-60% MeCN (0.1% TFA) in water (0.1% TFA) over 20 min. The desired fractions were poured into 10% Na$_2$CO$_3$ and extracted with dichloromethane (DCM) (8×10 mL). The combined DCM layers were dried over MgSO$_4$ and concentrated in vacuo to give 4-(3-(1-(7-chloroquinolin-2-yl)piperidin-4-yl)pyrazin-2-yl)-2-fluoro-N-methylbenzamide (135 mg, 0.284 mmol, 38.2% yield), as an off white solid. m/z=476 (M+1). $^1$H NMR (300 MHz, CDCl$_3$) δ 8.54 (d, J=2.34 Hz, 1H), 8.49 (d, J=2.34 Hz, 1H), 8.27 (t, J=8.04 Hz, 1H), 7.83 (d, J=9.35 Hz, 1H), 7.67 (d, J=2.05 Hz, 1H), 7.49 (d, J=8.62 Hz, 1H), 7.44 (dd, J=1.46, 8.04 Hz, 1H), 7.35 (dd, J=1.46, 12.42 Hz, 1H), 7.15 (dd, J=2.05, 8.48 Hz, 1H), 6.98 (d, J=9.35 Hz, 1H), 6.79 (d, J=6.28 Hz, 1H), 4.68 (d, J=13.30 Hz, 2H), 3.16-3.31 (m, 1H), 3.09 (dd, J=0.80, 4.75 Hz, 3H), 2.86-3.02 (m, 2H), 2.01-2.19 (m, 2H), 1.82 (d, J=11.55 Hz, 2H).

Example 2

2-Fluoro-4-(3-(1-(7-Fluoroquinolin-2-Yl)Piperidin-4-Yl) Pyrazin-2-Yl)-N-Methylbenzamide

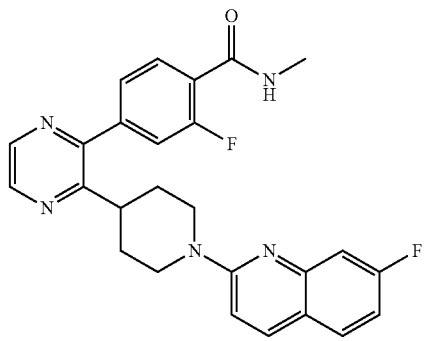

Scheme 2

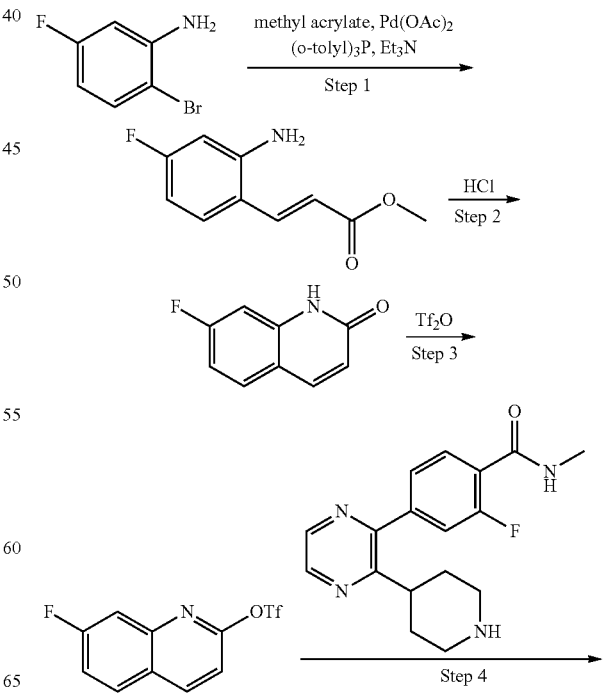

-continued

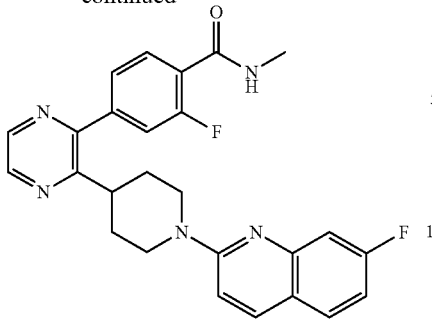

Step 1. (E)-Methyl 3-(2-Amino-4-Fluorophenyl)Acrylate

To a mixture of 2-bromo-5-fluoroaniline (35.00 g, 184 mmol, Aldrich), palladium (II) acetate (2.06 g, 9.18 mmol, Strem) and tri(o-tolyl)phosphine (5.60 g, 18.40 mmol; Strem) in acetonitrile (350 ml) at RT was added methyl acrylate (33.00 ml, 365 mmol, Aldrich) and triethylamine (64.00 ml, 460 mmol, Aldrich). The reaction was heated at 80° C. for 24 h. The reaction mixture was diluted with EtOAc (500 mL) and the resulting colorless crystalline solid was filtered and washed with EtOAc. The organic solution was concentrated to dryness and the solids were slurried in 10% EtOAc/hexane at 60° C. for 1 h. The slurry was cooled to RT and filtered. The solid was washed with 10% EtOAc/hexane and sucked dry with air to give 18.30 g (51%) of a light-yellow crystalline solid. m/z=195.9 (M+1).

Step 2. 7-Fluoroquinolin-2(1H)-One

A mixture of (E)-methyl 3-(2-amino-4-fluorophenyl)acrylate (30.38 g, 156 mmol) in THF (400 mL) and 3M hydrochloric acid (400 mL) was heated at 65° C. for 20 h. The mixture was cooled to RT and poured onto ice. The resulting precipitate was filtered, washed with copious amounts of water and dried in vacuo to give 20.65 g (81%) of a light-yellow amorphous solid. m/z=164 (M+1).

Step 3. 7-Fluoroquinolin-2-Yl Trifluoromethanesulfonate

To a cooled (0° C.) solution of 7-fluoroquinolin-2(1H)-one (1.60 g, 9.81 mmol) in pyridine (40 mL) was added trifluoromethanesulfonic anhydride (2.2 mL, 13.10 mmol, Aldrich) via syringe. After complete addition, the reaction was allowed to warm to RT and stirred for 1 h. The solvent was removed in vacuo and the residue was azeotroped with toluene. The residue was stirred vigorously over $Et_2O$, filtered and washed with $Et_{2O}$. The filtrate was concentrated to dryness to give 2.50 g (86%) of an orange oil. m/z=295.9 (M+1).

Step 4. 2-Fluoro-4-(3-(1-(7-Fluoroquinolin-2-Yl)Piperidin-4-Yl)Pyrazin-2-Yl)-N-Methylbenzamide To a RT solution of 2-fluoro-N-methyl-4-(3-(piperidin-4-yl)pyrazin-2-yl)benzamide trihydrochloride (1.00 g, 3.18 mmol, prepared according to Step 2 of Example 1) and triethylamine (2.00 ml, 14.35 mmol) in DMSO (10 ml) was added a solution of 7-fluoroquinolin-2-yl trifluoromethanesulfonate (1.10 g, 3.73 mmol, prepared according to Step 3 of Example 2) in DMSO (2 mL). The reaction mixture was heated at 60° C. for 2.5 h. The reaction was cooled RT and diluted with water. The mixture was extracted with $CH_2Cl_2$ (3×). The combined organic layers were washed with brine and dried over $Na_2SO_4$. The solution was filtered and the solution was evaporated onto silica gel and purified by flash chromatography (Isco (80 gram)) eluting with EtOAc:hexanes (0:1→3:1). The fractions containing product were concentrated in vacuo and the residue was stirred vigorously over $Et_2O$ for 3 h. The solid was filtered, washed with $Et_2O$ and dried to give 674 mg (46%) of the desired product. m/z=460 (M+1). $^1$H NMR (300 MHz, DMSO-$d_6$) δ ppm 8.62 (d, J=2.34 Hz, 1H), 8.59 (d, J=2.34 Hz, 1H), 8.39 (br. s., 1H), 8.04 (d, J=9.21 Hz, 1H), 7.69-7.83 (m, 2H), 7.45-7.58 (m, 2H), 7.18-7.28 (m, 2H), 7.08 (td, J=8.77, 2.63 Hz, 1H), 4.66 (d, J=13.30 Hz, 2H), 3.13-3.29 (m, 1H), 2.86-3.03 (m, 2H), 2.82 (d, J=4.68 Hz, 3H), 1.72-1.97 (m, 4H).

Example 3

2-Fluoro-N-Methyl-4-(3-(1-(Quinolin-2-Yl)Piperidin-4-Yl)Pyrazin-2-Yl)Benzamide

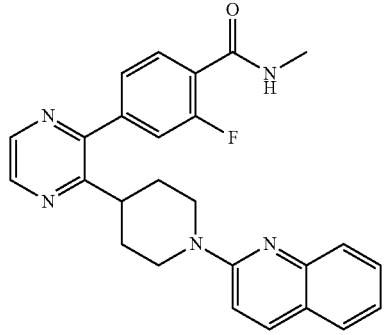

The title compound was prepared in an analogous manner to Example 1 by using 7-chloroquinoline in place of 2,7-dichloroquinoline in Step 3 to give 2-fluoro-N-methyl-4-(3-(1-(quinolin-2-yl)piperidin-4-yl)pyrazin-2-yl)benzamide (49 mg, 0.111 mmol, 23.5% yield), as a light yellow solid. m/z=442 (M+1). $^1$H NMR (300 MHz, CDCl$_3$) δ ppm 8.54 (d, J=2.34 Hz, 1H), 8.49 (d, J=2.34 Hz, 1H), 8.26 (t, J=8.04 Hz, 1H), 7.88 (d, J=9.21 Hz, 1H), 7.69 (d, J=8.33 Hz, 1H), 7.59 (d, J=8.04 Hz, 1H), 7.52 (dt, J=1.46, 7.67 Hz, 1H), 7.44 (dd, J=1.53, 7.97 Hz, 1H), 7.36 (dd, J=1.53, 12.35 Hz, 1H), 7.15-7.25 (m, 1H), 7.01 (d, J=9.21 Hz, 1H), 6.78 (br. s., 1H), 4.68 (d, J=13.15 Hz, 2H), 3.14-3.29 (m, 1H), 3.03-3.14 (m, 3H), 2.82-3.03 (m, 2H), 2.03-2.23 (m, 2H), 1.83 (d, J=11.84 Hz, 2H).

Example 4

2-Fluoro-4-(3-(1-(6-Fluoroquinolin-2-Yl)Piperidin-4-Yl)Pyrazin-2-Yl)-N-Methylbenzamide

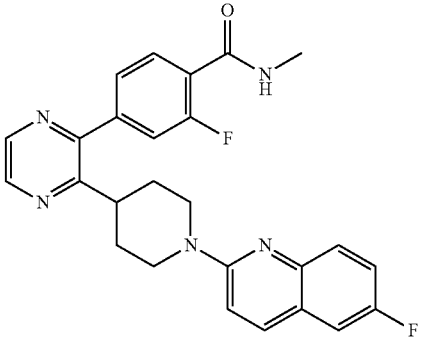 [SMILES: CNC(=O)c1ccc(-c2nccnc2C2CCN(c3ccc4cc(F)ccc4n3)CC2)cc1F]

To a solution of 2-fluoro-N-methyl-4-(3-(piperidin-4-yl)pyrazin-2-yl)benzamide (155 mg, 0.493 mmol, prepared according to Step 2 of Example 1), 2-chloro-6-fluoroquinoline (108 mg, 0.595 mmol, Combi-blocks), and DMSO (2 mL) was added potassium carbonate (240 mg, 1.737 mmol). The solution was stirred at 100° C. After 72 h, the reaction was allowed to cool to room temperature and diluted with water (50 mL). After stirring for 30 min, the solution was filtered and the filtered solid adsorbed onto a plug of silica gel and chromatographed through a Redi-Sep® pre-packed silica gel column (12 g), eluting with 0-80% EtOAc in hexane, to provide a light yellow solid, which contained residual DMSO as measure by NMR. The solids were redissolved in diethyl ether and washed with water, brine, and concentrated in vacuo to give 2-fluoro-4-(3-(1-(6-fluoroquinolin-2-yl)piperidin-4-yl)pyrazin-2-yl)-N-methylbenzamide (90 mg, 0.196 mmol, 39.7% yield), as a light yellow solid. m/z=460 (M+1). $^1$H NMR (300 MHz, CDCl$_3$) δ ppm 8.55 (d, J=2.48 Hz, 1H), 8.49 (d, J=2.48 Hz, 1H), 8.26 (t, J=8.04 Hz, 1H), 7.82 (d, J=9.21 Hz, 1H), 7.65 (dd, J=5.26, 9.06 Hz, 1H), 7.44 (dd, J=1.61, 8.04 Hz, 1H), 7.36 (dd, J=1.61, 12.42 Hz, 1H), 7.28-7.32 (m, 1H), 7.22 (dd, J=2.92, 8.92 Hz, 1H), 7.04 (d, J=9.21 Hz, 1H), 6.77 (br. s., 1H), 4.64 (d, J=13.45 Hz, 2H), 3.14-3.31 (m, 1H), 3.03-3.14 (m, 3H), 2.81-3.02 (m, 2H), 2.05-2.21 (m, 2H), 1.82 (d, J=11.69 Hz, 2H).

Example 5

2-Fluoro-4-(3-(1-(8-Fluoroquinolin-2-Yl)Piperidin-4-Yl)Pyrazin-2-Yl)-N-Methylbenzamide

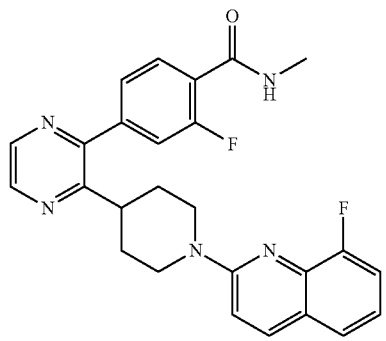

The title compound was prepared analogously to Example 8 by using 2-chloro-8-fluoroquinoline (Combi-blocks) and 2-fluoro-N-methyl-4-(3-(piperidin-4-yl)pyrazin-2-yl)benzamide trihydrochloride (prepared according to Step 2 of Example 1) in Step 3. $^1$H NMR (400 MHz, CHLOROFORM-d) δ ppm 1.85 (d, J=11.93 Hz, 2H) 2.04-2.19 (m, 2H) 2.91-3.03 (m, 2H) 3.09 (d, J=4.50 Hz, 3H) 3.22 (tt, J=11.61, 3.74 Hz, 1H) 4.72 (d, J=13.50 Hz, 2H) 6.80 (d, J=7.43 Hz, 1H) 7.05 (d, J=9.19 Hz, 1H) 7.08-7.15 (m, 1H) 7.20-7.25 (m, 1H) 7.32-7.39 (m, 2H) 7.44 (dd, J=8.02, 1.37 Hz, 1H) 7.88 (dd, J=9.19, 1.17 Hz, 1H) 8.27 (t, J=8.02 Hz, 1H) 8.50 (d, J=2.35 Hz, 1H) 8.55 (d, J=2.35 Hz, 1H). m/z=460 (M+1).

Example 6

2-Fluoro-N-Methyl-4-(3-(1-(Quinazolin-2-Yl)Azetidin-3-Yl)Pyrazin-2-Yl)Benzamide

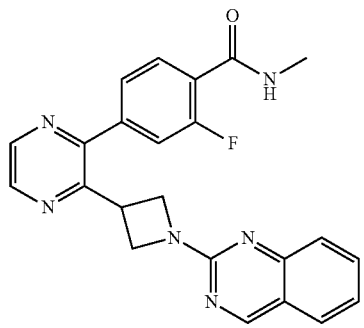 [SMILES: CNC(=O)c1ccc(-c2nccnc2C2CN(c3ccc4ccccc4n3)C2)cc1F]

Scheme 3

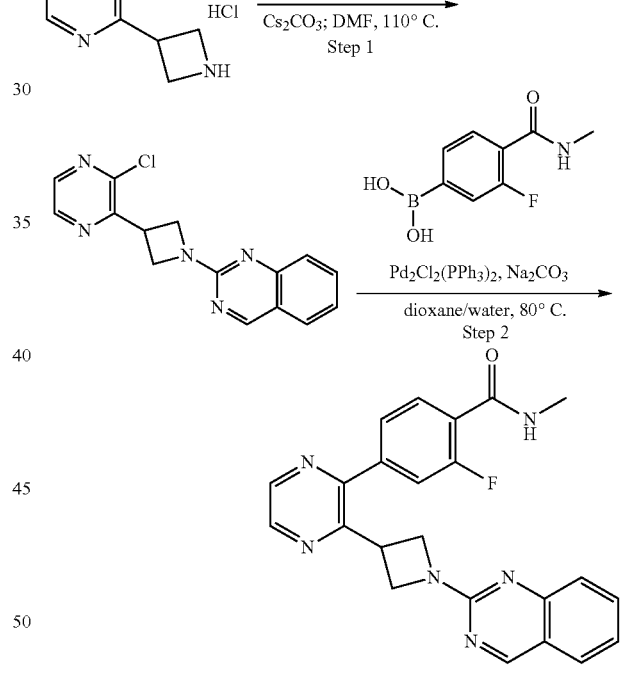

Step 1. 2-(3-(3-Chloropyrazin-2-Yl)Azetidin-1-Yl)Quinazoline 2-(Azetidin-3-yl)-3-chloropyrazine hydrochloride (1.50 g, 7.28 mmol), 2-chloroquinazoline (1.20 g, 7.28 mmol, Parkway Scientific), and cesium carbonate (5.22 g, 16.0 mmol, Fluka) were mixed in DMF (30 mL) in a round bottom flask under a nitrogen atmosphere. The mixture was stirred at 110° C. for 17 h. The reaction mixture was cooled to room temperature, diluted with water, and extracted with EtOAc (2×). The combined organic extracts were washed with saturated sodium chloride, dried over magnesium sulfate, filtered, and concentrated in vacuo. The resulting crude mixture was purified via silica gel flash column chromatography eluting with 0% to 100% EtOAc in hexanes to give 1.02 g (47%) of a yellow amorphous solid. $^1$H NMR (400 MHz, CHLOROFORM-d) δ ppm 4.41-4.50 (m, 1H) 4.58-4.63 (m, 2H) 4.65-4.72 (m, 2H) 7.22-7.28 (m, 1H) 7.61-7.72 (m, 3H) 8.28 (d, J=2.35 Hz, 1H) 8.51 (d, J=2.35 Hz, 1H) 9.04 (s, 1H). m/z=298 (M+1).

Step 2. 2-Fluoro-N-Methyl-4-(3-(1-(Quinazolin-2-Yl)Azetidin-3-Yl)Pyrazin-2-Yl)Benzamide (0.400 g, 1.34 mmol), (3-fluoro-4-(methylcarbamoyl)phenyl)boronic acid (0.318 g, 1.61 mmol, Combi-Blocks), and trans-dichlorobis(triphenylphosphine)palladium (ii) (0.019 g, 0.027 mmol, Strem) were mixed in 1,4-Dioxane (6 mL) in a round bottom flask under an argon atmosphere. Sodium carbonate (2.02 mL, 4.03 mmol, 2.0 M aqueous solution) was added, and the reaction mixture was stirred at 80° C. for 3.5 h. The reaction mixture was cooled to room temperature, diluted with water, and extracted with EtOAc. The organic layer was separated, washed with saturated sodium chloride, dried over magnesium sulfate, filtered, and concentrated in vacuo. The resulting crude mixture was purified via silica gel flash column chromatography eluting with 50% to 100% EtOAc in hexanes to give 557 mg (86%) of the title compound as a light yellow solid. $^1$H NMR (400 MHz, CHLOROFORM-d) δ ppm 3.09 (d, J=4.69 Hz, 3H) 4.29-4.39 (m, 1H) 4.48-4.58 (m, 4H) 6.75-6.86 (br. m., 1H) 7.22-7.28 (m, 1H) 7.36 (d, J=12.52 Hz, 1H) 7.41 (dd, J=8.02, 1.17 Hz, 1H) 7.60-7.72 (m, 3H) 8.27 (t, J=8.02 Hz, 1H) 8.57 (d, J=2.15 Hz, 1H) 8.65 (d, J=2.15 Hz, 1H) 9.02 (s, 1H). m/z=415 (M+1).

Example 7

2-Fluoro-N-Methyl-4-(3-(1-(Quinolin-2-Yl)Azetidin-3-Yl) Pyrazin-2-Yl)Benzamide

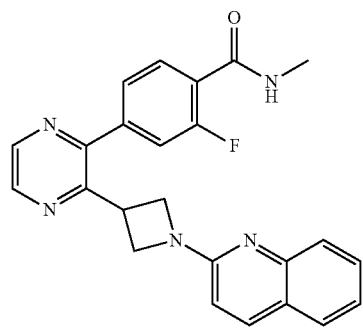

A mixture of 2-(3-(3-chloropyrazin-2-yl)azetidin-1-yl) quinoline (0.072 g, 0.243 mmol; see preparation in WO2011143365), (3-fluoro-4-(methylcarbamoyl)phenyl) boronic acid (0.076 g, 0.388 mmol, Combi-blocks), potassium phosphate (0.129 g, 0.607 mmol, Alfa Aesar), bis(di-tert-butyl(4-dimethylaminophenyl)phosphine) dichloropalladium (II) (0.017 g, 0.024 mmol, Aldrich), water (0.3 mL) and dioxane (1.2 mL) was purged with Argon gas. The mixture was heated at 100° C. for 30 min in microwave reactor, then the heating was stopped and the mixture was cooled to room temperature. The mixture was diluted with saturated Na$_2$CO$_3$ and extracted with EtOAc three times. The organic layer was dried over Na$_2$SO$_4$ and concentrated in vacuo. The crude was purified by silica gel chromatography (12 g, 0%-100% EtOAc-CH$_2$Cl$_2$). The product was further purified by reverse phase HPLC (Shimazu; Gemini 10 μM C18 110A AXIA, 100×50 mm column, 10-55% MeCN in water with 0.1% TFA in 26 min) The collected fractions were neutralized with solid Na$_2$CO$_3$ and extracted with CH$_2$Cl$_2$ three times. The organic phase was dried over Na$_2$SO$_4$ and concentrated in vacuo. The product was obtained as a white solid (73 mg, 73%). $^1$H NMR (400 MHz, CHLOROFORM-d) δ ppm 3.10 (d, J=4.69 Hz, 3H) 4.30-4.55 (m, 5H) 6.63 (d, J=8.80 Hz, 1H) 6.83 (d, J=7.04 Hz, 1H) 7.23 (t, J=7.34 Hz, 1H) 7.37 (d, J=12.32 Hz, 1H) 7.42 (dd, J=8.02, 1.17 Hz, 1H) 7.50-7.57 (m, 1H) 7.61 (d, J=7.82 Hz, 1H) 7.73 (d, J=8.41 Hz, 1H) 7.89 (d, J=8.80 Hz, 1H) 8.28 (t, J=8.02 Hz, 1H) 8.57 (d, J=2.35 Hz, 1H) 8.64 (d, J=2.35 Hz, 1H). m/z=414 (M+1).

Example 8

2-Fluoro-4-(3-(1-(7-Fluoroquinolin-2-Yl)Azetidin-3-Yl) Pyrazin-2-Yl)-N-Methylbenzamide

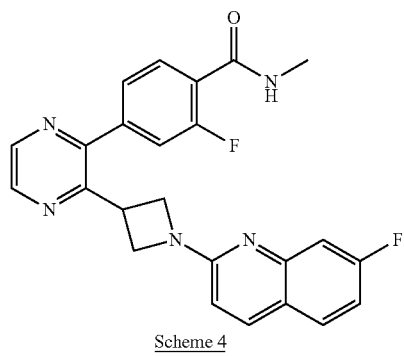

Scheme 4

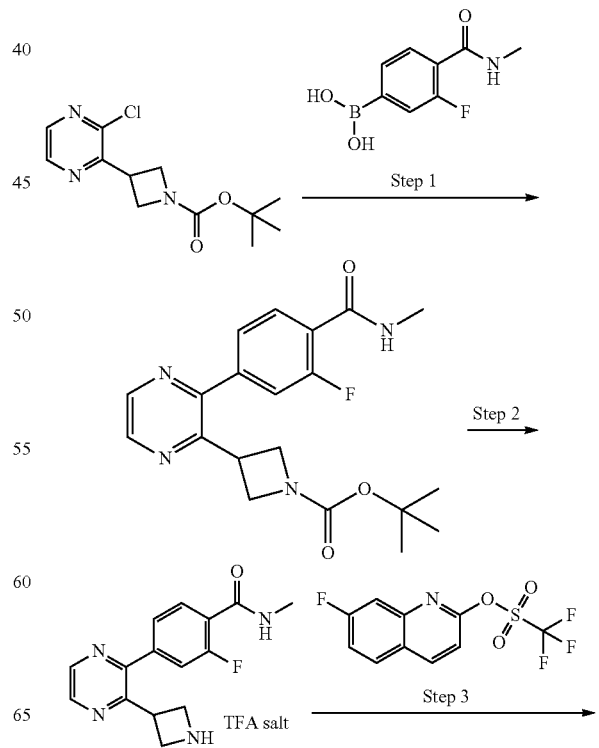

-continued

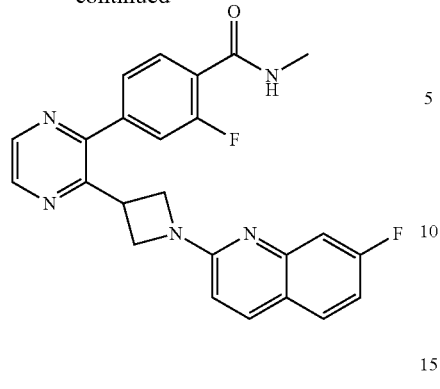

Step 1: Tert-Butyl 3-(3-(3-Fluoro-4-(Methylcarbamoyl)Phenyl) Pyrazin-2-Yl)Azetidine-1-Carboxylate The compound was prepared analogously to Example 1 by using (3-fluoro-4-(methylcarbamoyl)phenyl)boronic acid (purchased from Combi Blocks) and tert-butyl 3-(3-chloropyrazin-2-yl)azetidine-1-carboxylate. m/z=287 (M+1-100).

Step 2: 4-(3-(Azetidin-3-Yl)Pyrazin-2-Yl)-2-Fluoro-N-Methylbenzamide Tris(2,2,2-Trifluoroacetate)

To a mixture of tert-butyl 3-(3-(3-fluoro-4-(methylcarbamoyl)phenyl)pyrazin-2-yl)azetidine-1-carboxylate (5.19 g, 13.43 mmol), prepared according to Step 1 of Example 8, and CH$_2$Cl$_2$ (20 mL) was added trifluoroacetic acid (7.24 mL, 94.00 mmol). The mixture was stirred at room temperature for 1 h. LCMS showed the product. The mixture was concentrated in vacuo. CH$_2$Cl$_2$ was added and evaporated to remove extra TFA. Ether was added and evaporated. The product was obtained as a yellow oil after drying on vacuum overnight and used in next step without purification. m/z=287 (M+1).

Step 3: 2-Fluoro-4-(3-(1-(7-Fluoroquinolin-2-Yl)Azetidin-3-Yl)Pyrazin-2-Yl)-N-Methylbenzamide A mixture of 4-(3-(azetidin-3-yl)pyrazin-2-yl)-2-fluoro-N-methylbenzamide tris(2,2,2-trifluoroacetate) (0.953 g, 1.517 mmol), potassium carbonate (0.839 g, 6.070 mmol), 7-fluoroquinolin-2-yl trifluoromethanesulfonate (0.537 g, 1.821 mmol, prepared according to Step 3 of Example 2), and DMSO (10 mL) was stirred at 50° C. for 1 h. LCMS showed the product and no more azetidine starting material. The mixture was diluted with water and extracted with CH$_2$Cl$_2$ three times. The organic layer was dried over Na$_2$SO$_4$ and concentrated in vacuo. The crude was purified by silica gel chromatography: 40 g, 5-100% EtOAc-hexane. The impurity 2-hydroxyquinoline was further removed by trituration with CH$_2$Cl$_2$ and hexane twice. The product was obtained as a white solid (510 mg, 78%). $^1$H NMR (400 MHz, CHLOROFORM-d) δ ppm 3.09 (d, J=4.50 Hz, 3H) 4.33-4.50 (m, 5H) 6.56 (d, J=9.00 Hz, 1H) 6.81 (d, J=7.04 Hz, 1H) 6.98 (td, J=8.61, 2.54 Hz, 1H) 7.31-7.45 (m, 3H) 7.56 (dd, J=8.71, 6.36 Hz, 1H) 7.84 (d, J=9.00 Hz, 1H) 8.28 (t, J=8.02 Hz, 1H) 8.57 (d, J=2.15 Hz, 1H) 8.64 (d, J=2.35 Hz, 1H). m/z=432 (M+1).

Example 9

2-Fluoro-4-(3-(1-(7-Fluoroquinazolin-2-Yl)Azetidin-3-Yl)Pyrazin-2-Yl)-N-Methylbenzamide

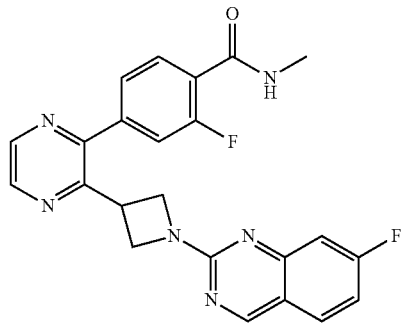

The title compound was prepared analogously to Example 8 by using 2-chloro-7-fluoroquinazoline (Activate Scientific) in Step 3. $^1$H NMR (400 MHz, CHLOROFORM-d) δ ppm 3.01-3.15 (m, 3H) 4.25-4.40 (m, 1H) 4.43-4.61 (m, 4H) 6.99 (td, J=8.71, 2.15 Hz, 1H) 7.23 (dd, J=10.66, 1.86 Hz, 1H) 7.31-7.45 (m, 2H) 7.67 (dd, J=8.61, 6.26 Hz, 1H) 8.27 (t, J=8.02 Hz, 1H) 8.57 (d, J=2.15 Hz, 1H) 8.66 (d, J=2.15 Hz, 1H) 8.96 (s, 1H). m/z=433 (M+1).

Example 10

4-(3-(1-(7-Chloroquinazolin-2-Yl)Azetidin-3-Yl)Pyrazin-2-Yl)-2-Fluoro-N-Methylbenzamide

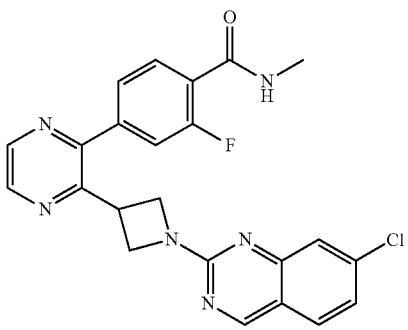

Scheme 5

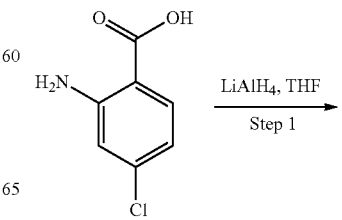

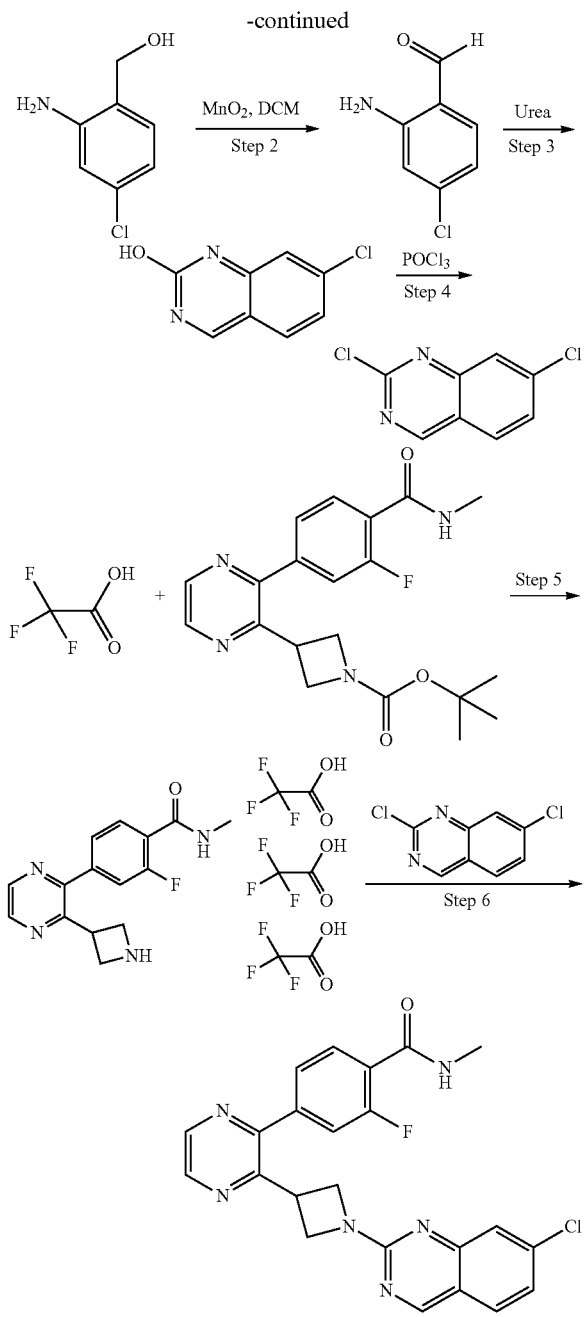

Steps 1-4: 2,7-Dichloroquinazoline

Step 1: (2-Amino-4-Chlorophenyl)Methanol

In a 500 mL round bottom flask, the stirred solution of 2-amino-4-chlorobenzoic acid (42.8 g, 250.29 mmol, Aldrich) was dissolved anhydrous THF (200 mL) and the solution was cooled in an ice-bath. Lithium aluminum hydride (11.76 g, 312.86 mmol) was added portionwise to the above solution at the ice-bath temperature under nitrogen atmosphere. The resulting mixture was stirred at rt for 8 h. On completion of reaction the reaction mixture was cooled to ice-bath temperature and quenched by sequential addition of cold water (12 mL), 15% NaOH (12 mL) and water (36 mL). The resulting slurry was stirred at rt for 30 min and filtered through a CELITE™ pad. The solid residue was washed with ethyl acetate (1000 mL) and combined filtrate was concentrated under reduced pressure to give (2-amino 4-chlorophenyl)methanol as an off white solid. Yield: 32 g (81.6%). LCMS (ESI, m/z): 181 (M+23)$^+$ Step 2. 2-Amino-4-Chlorobenzaldehyde In a 2 L 3-neck round bottom flask, the stirred solution of (2-amino-4-chlorophenyl)methanol 2 (32 g, 203.82 mmol) in DCM (765 mL), manganese (IV) oxide (150 g, 1.724 mol) was added at rt. The resulting reaction mixture was stirred at rt under argon atmosphere for 40 h. On completion of reaction the reaction mixture was filtered through CELITE™ pad and solid residue was washed thoroughly with DCM (1000 mL). The combined filtrate was concentrated under reduced pressure to give 2-amino-4-chlorobenzaldehyde as orange solid. Yield: 24 g (76.2%).

Step 3: 7-Chloroquinazolin-2-Ol

In a 500 mL round bottom flask, the uniform mixture of 2-amino-4-chlorobenzaldehyde (16 g, 103.2 2 mmol) and urea (123.8 g, 2063 mmol) was heated at 170° C. with vigorous stirring for 2 h. On completion of reaction, the reaction mixture was cooled to rt and diluted with ice-cold water. The solid that formed was collected by filtration and washed with ice-cold water. The solid was dried under reduced pressure to give crude 7-chloroquinazolin-2-ol as a yellow solid. Yield: 19 g. LCMS (ESI, m/z): 181 (M+1)+

Step 4: 2,7-Dichloroquinazoline

In a 250 mL three neck round bottom flask, 7-chloroquinazolin-2-ol (19 g, 105.55 mmol) was suspended in freshly distilled POCl$_3$ (190 mL) at rt. The resulting suspension was heated to 110° C. for 4 h. On completion of reaction, the reaction mixture was cooled to rt and concentrated under reduced pressure. The residue obtained was diluted with ethyl acetate (200 mL) and cold water (200 mL). The organic layer was separated and the aqueous phase was re-extracted with ethyl acetate (500 mL×2). The combined EtOAc extract was washed with brine and concentrated under reduced pressure. The residue (pale brown) obtained was purified by silica gel (60-120 mesh) column chromatography and gradient elution with 12-20% ethyl acetate-hexanes gave 2,7-dichloroquinazoline as a pale yellow solid. Yield: 7 g (33.5%). LCMS (ESI, m/z): 199 (M+1)$^+$.

Step 5: 4-(3-(Azetidin-3-Yl)Pyrazin-2-Yl)-2-Fluoro-N-Methylbenzamide Tris(2,2,2-Trifluoroacetate)

To a mixture of tert-butyl 3-(3-(3-fluoro-4-(methylcarbamoyl)phenyl)pyrazin-2-yl)azetidine-1-carboxylate (5.19 g, 13.43 mmol) and DCM (20 mL) was added 2,2,2-trifluoroacetic acid (7.24 mL, 94 mmol). The mixture was stirred at rt for 1 h. The mixture was concentrated in vacuo. DCM was added and evaporated to remove extra TFA. Ether was added and evaporated. The product was obtained as a yellow oil after drying on vacuum overnight. MS: 287 (M+1).

Step 6: 4-(3-(1-(7-Chloroquinazolin-2-Yl)Azetidin-3-Yl)Pyrazin-2-Yl)-2-Fluoro-N-Methylbenzamide 4-(3-(Azetidin-3-yl)pyrazin-2-yl)-2-fluoro-N-methylbenzamide tris(2,2,2-trifluoroacetate) (0.150 g, 0.239 mmol), 2,7-dichloroquinazoline (0.062 g, 0.310 mmol), and potassium carbonate (0.165 g, 1.19 mmol, Aldrich) were mixed in butan-1-ol (2 mL) in a sealed tube. The reaction mixture was stirred at 110° C. for 18 h. The reaction mixture was cooled to room temperature, diluted with water, and extracted with EtOAc. The organic layer was separated, washed with saturated sodium chloride, dried over magnesium sulfate, filtered, and concentrated in vacuo. The resulting crude mixture was purified via silica gel flash column chromatography eluting with 50% to 100% EtOAc in hexanes to yield give 99 mg (92%) of a light yellow solid. $^1$H NMR (400 MHz, CHLOROFORM-d) δ ppm 3.09 (d, J=4.50 Hz, 3H) 4.29-4.38 (m, 1H) 4.46-4.58 (m, 4H) 6.75-6.85 (br. m., 1H) 7.18 (dd, J=8.61, 1.56 Hz, 1H) 7.36 (d, J=12.32 Hz, 1H) 7.40 (dd, J=8.12, 1.27 Hz, 1H) 7.60 (d, J=8.41 Hz, 1H) 7.63 (br. s., 1H) 8.27 (t, J=8.02 Hz, 1H) 8.57 (d, J=2.15 Hz, 1H) 8.65 (d, J=2.15 Hz, 1H) 8.97 (s, 1H). m/z=449 (M+1).

Example 11

2-Fluoro-4-(3-(1-(6-Fluoroquinazolin-2-Yl)Azetidin-3-Yl)Pyrazin-2-Yl)-N-Methylbenzamide

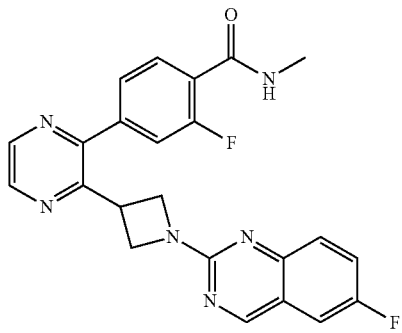

The title compound was prepared analogously to Example 8 by using 6-fluoroquinazolin-2-yl trifluoromethanesulfonate in place of 7-fluoroquinolin-2-yl trifluoromethanesulfonate in Step 3 and purified by reverse phase HPLC. The pure fractions were concentrated to minimal $H_2O$, neutralized by saturated aqueous $NaHCO_3$. The solid was collected by filtration, washed with $H_2O$ to give the title compound (49 mg, 51%). $^1$H NMR (400 MHz, DMSO-$d_6$) δ ppm 9.19 (1H, s), 8.73 (1H, d, J=2.3 Hz), 8.67 (1H, d, J=2.3 Hz), 8.32-8.45 (1H, m), 7.78 (1H, t, J=7.6 Hz), 7.62-7.71 (2H, m), 7.51-7.62 (2H, m), 7.49 (1H, dd, J=7.9, 1.5 Hz), 4.23-4.47 (5H, m), 2.82 (3H, d, J=4.5 Hz). m/z=433 (M+1).

Example 12

4-(3-(1-(7-Chloro-6-Fluoroquinazolin-2-Yl)Azetidin-3-Yl)Pyrazin-2-Yl)-2-Fluoro-N-Methylbenzamide

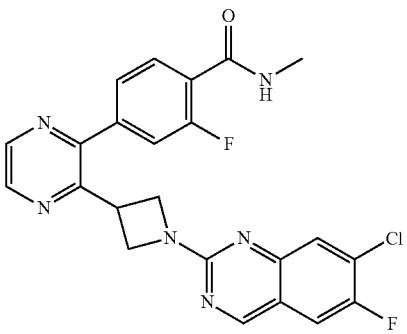 [SMILES: CNC(=O)c1ccc(-c2nccnc2C2CN(c3ncc4cc(F)c(Cl)cc4n3)C2)cc1F]

Scheme 6

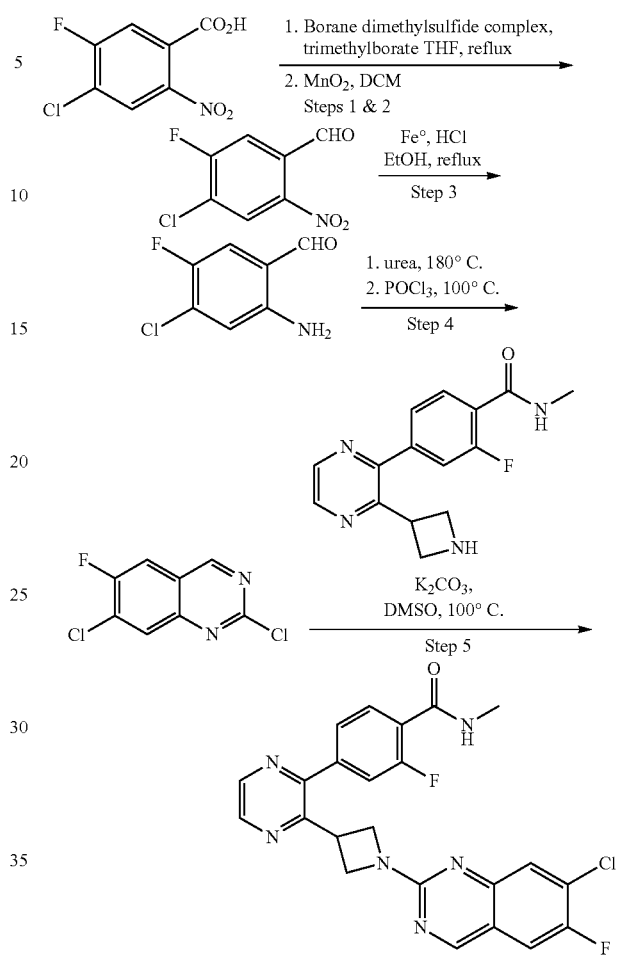

Step 1 & 2: 4-Chloro-5-Fluoro-2-Nitrobenzaldehyde

STEP 1. Borane methyl sulfide, complex (2.81 mL, 29.7 mmol) was added via syringe to a solution of trimethyl borate (26.5 mL, 237 mmol) and 4-chloro-5-fluoro-2-nitrobenzoic acid (6.51 g, 29.7 mmol) in THF (75 mL) under argon. The mixture was stirred at reflux for 6 h, then cooled to 0° C. MeOH (50 mL) was added dropwise and the mixture was stirred for 30 min at RT. The solvent was then removed in vacuo and the resulting oil was purified by silica gel to give alcohol as a solid, which was taken directly to the next step.

STEP 2. The material produced above was dissolved in DCM 100 mL and manganese (iv) oxide (2.58 g, 29.7 mmol) was added. The mixture was stirred overnight at RT, and then the manganese (iv) oxide was removed by filtration though CELITE™. The Titrate was then concentrated in vacuo and purified by silica gel chromatography to give 4-chloro-5-fluoro-2-nitrobenzaldehyde as a yellow solid. (1.32 g, 78% yield for 2 steps). $^1$H NMR (400 MHz, DMSO-$d_6$) δ ppm 7.94 (d, J=8.80 Hz, 1H) 8.55 (d, J=6.26 Hz, 1H) 10.18 (d, J=1.96 Hz, 1H).

Step 3. 2-Amino-4-Chloro-5-Fluorobenzaldehyde

A mixture of 4-chloro-5-fluoro-2-nitrobenzaldehyde (1.50 g, 7.37 mmol), concentrated hydrochloric acid (0.30 ml, 3.68 mmol), and iron (1.32 g, 23.6 mmol) in EtOH (18 mL), AcOH (18 mL), and water (9 mL) was heated to reflux for 30 minutes, then cooled to RT. The resulting suspension was filtered through CELITE™ and the filtrate was then partitioned between EtOAc and water. The layers were separated, the organic layer was washed with saturated aqueous sodium bicarbonate solution, dried over anhydrous magnesium sulfate, filtered, and concentrated in vacuo to give 2-amino-4-chloro-5-fluorobenzaldehyde as a yellow solid (1.15 g, 90% yield). m/z=174 (M+1).

Step 4. 2,7-Dichloro-6-Fluoroquinazoline

A mixture of 2-amino-4-chloro-5-fluorobenzaldehyde (0.30 g, 1.73 mmol) and urea (1.04 g, 17.3 mmol) was heated to 180° C. for 1 h, then cooled to RT. The solid was then suspended in a mixture of EtOAc and water and then it was filtered and the collected solid was washed with water several times, then air-dried. This intermediate quinazolinone was then suspended in phosphorus oxychloride (3.0 mL, 32.2 mmol) and then heated to 100° C. for 1 h. After cooling to RT, the mixture was added dropwise to an ice-water mixture. The mixture was stirred for 5 minutes and then the product was extracted into EtOAc (3×). The combined extracts were dried over anhydrous magnesium sulfate, filtered, and concentrated in vacuo to give an oil that was purified by silica gel chromatography to give 2,7-dichloro-6-fluoroquinazoline as a white solid (46 mg, 12% yield). m/z=217 (M+1).

Step 5. 4-(3-(1-(7-Chloro-6-Fluoroquinazolin-2-Yl) Azetidin-3-Yl) Pyrazin-2-Yl)-2-Fluoro-N-Methyl-benzamide A mixture of 2,7-dichloro-6-fluoroquinazoline (46 mg, 0.21 mmol), 4-(3-(azetidin-3-yl)pyrazin-2-yl)-2-fluoro-N-methylbenzamide tris(2,2,2-trifluoroacetate) (0.15 g, 0.23 mmol), and potassium carbonate (0.15 g, 1.06 mmol) in DMSO (1 mL) was heated to 100° C. for 1 h, then cooled to RT. Water was added, then the product was extracted into EtOAc. The combined extracts were washed with water (2×), dried over anhydrous magnesium sulfate, filtered, and concentrated in vacuo to give an oil. This oil was purified by silica gel chromtography to give 4-(3-(1-(7-Chloro-6-fluoro-quinazolin-2-yl)azetidin-3-yl)pyrazin-2-yl)-2-fluoro-N-methylbenzamide as a light yellow solid (69 mg, 70% yield). m/z=467 (M+1). $^1$H NMR (400 MHz, CHLOROFORM-d) δ ppm 3.09 (d, J=4.70 Hz, 3H) 4.28-4.38 (m, 1H) 4.45-4.54 (m, 4H) 6.80 (br. s., 1H) 7.32-7.42 (m, 3H) 7.71 (d, J=6.65 Hz, 1H) 8.27 (t, J=7.92 Hz, 1H) 8.58 (d, J=1.76 Hz, 1H) 8.65 (s, 1H) 8.94 (s, 1H).

Example 13

2-Fluoro-4-(3-(1-(6-Fluoroquinolin-2-Yl)Azetidin-3-Yl) Pyrazin-2-yl)-N-Methylbenzamide

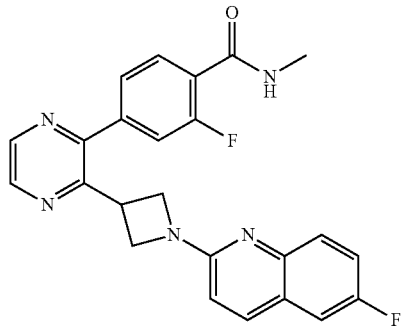 [SMILES: CNC(=O)c1ccc(-c2nccnc2C2CN(c3ccc4cc(F)ccc4n3)C2)cc1F]

The title compound was prepared analogously to Example 8 by using 2-chloro-6-fluoroquinoline (Combi-blocks) in Step 3. $^1$H NMR (400 MHz, CHLOROFORM-d) δ ppm 3.09 (dd, J=4.79, 0.68 Hz, 3H) 4.20-4.56 (m, 5H) 6.65 (d, J=9.00 Hz, 1H) 6.80 (d, J=6.65 Hz, 1H) 7.21-7.33 (m, 2H) 7.36 (dd, J=12.32, 1.57 Hz, 1H) 7.42 (dd, J=8.12, 1.66 Hz, 1H) 7.70 (dd, J=9.10, 5.18 Hz, 1H) 7.83 (d, J=8.80 Hz, 1H) 8.28 (t, J=8.02 Hz, 1H) 8.56 (d, J=2.35 Hz, 1H) 8.64 (d, J=2.35 Hz, 1H). m/z=432 (M+1).

Example 14

4-(3-(1-(7-Chloro-1,5-Naphthyridin-2-Yl)Azetidin-3-Yl)Pyrazin-2-Yl)-2-Fluoro-N-Methylbenzamide

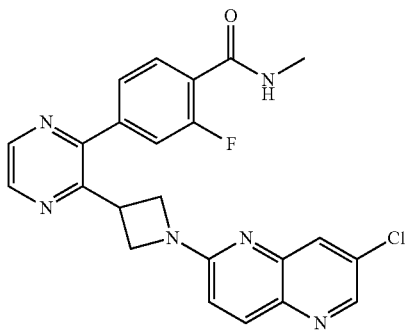

Scheme 7

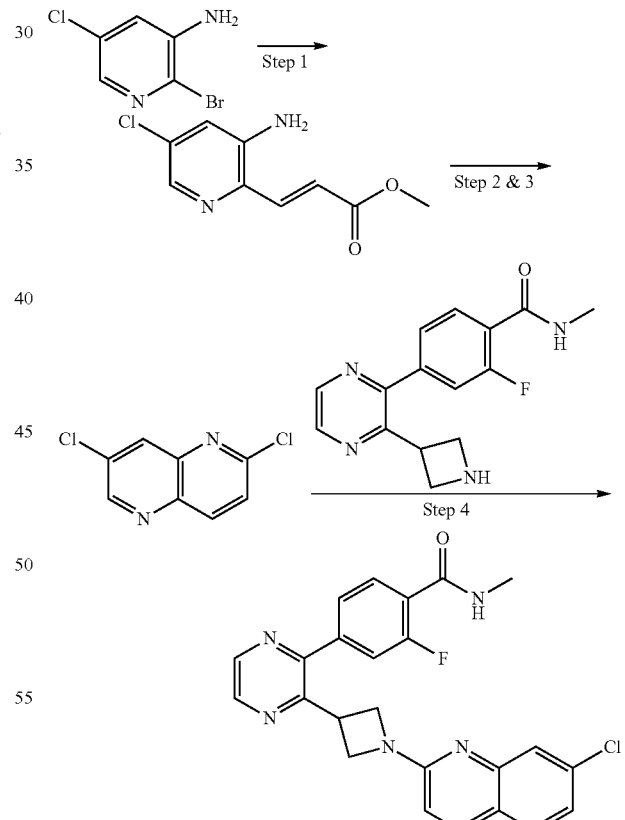

Step 1. (E)-Methyl 3-(3-Amino-5-Chloropyridin-2-Yl)Acrylate

A solution of 3-amino-2-bromo-5-chloropyridine (2.257 ml, 19.96 mmol), Reactant 2 (0.283 g, 0.399 mmol), triethylamine (3.03 g, 29.9 mmol) and methyl acrylate (3.44 g, 39.9 mmol) in 5 mL of DMF was heated at 145° C. under microwave irradiation for 35 min. The reaction mixture was evaporated to dryness and was loaded to flash column (DCM to DCM/EA=10:1) to give 1.98 g of pure (E)-methyl 3-(3-amino-5-chloropyridin-2-yl)acrylate (2.7 g, 12.70 mmol, 63.6% yield) as a light yellow solid and 820 mg of less pure product. $^1$H NMR (400 MHz, CHLOROFORM-d) δ ppm=8.01 (d, J=1.8 Hz, 1H), 7.72 (d, J=15.1 Hz, 1H), 7.01 (d, J=2.0 Hz, 1H), 6.92 (d, J=15.3 Hz, 1H), 4.02 (br. s., 2H), 3.81 (s, 3H).

Steps 2 & 3. 2,7-Dichloro-1,5-Naphthyridine

A suspension of (E)-methyl 3-(3-amino-5-chloropyridin-2-yl)acrylate (1.2 g, 5.64 mmol) and sodium methoxide (0.786 ml, 14.11 mmol) in 20 mL of ethanol was refluxed for 3 h until the starting material disappeared. The reaction mixture was evaporated to dryness to give crude product 7-chloro-1,5-naphthyridin-2(1H)-one. To the crude residue was added phosphorus oxychloride (5.17 ml, 56.4 mmol) and the resulting mixture was stirred at 70° C. for 4 h. The excess POCl$_3$ was removed under reduced pressure and the residue was directly submitted to flash column (DCM) to give 2,7-dichloro-1,5-naphthyridine (540 mg, 2.71 mmol, 48.1% yield) as an off-white solid. $^1$H NMR (400 MHz, CHLOROFORM-d) δ ppm=8.90 (d, J=2.2 Hz, 1H), 8.35 (d, J=8.8 Hz, 1H), 8.31 (d, J=1.8 Hz, 1H), 7.63 (d, J=8.8 Hz, 1H). m/z=199 (M+1).

Step 4. 4-(3-(1-(7-Chloro-1,5-Naphthyridin-2-Yl) Azetidin-3-Yl)Pyrazin-2-Yl)-2-Fluoro-N-Methyl-benzamide A mixture of 4-(3-(azetidin-3-yl)pyrazin-2-yl)-2-fluoro-N-methylbenzamide tetrakis(2,2,2-trifluoroacetate) (160 mg, 0.216 mmol), 2,7-dichloro-1,5-naphthyridine (47.2 mg, 0.237 mmol), cesium carbonate (86 μl, 1.078 mmol) and bis(tri-tert-butylphosphine)palladium (0) (3.30 mg, 6.47 μmol) in 1 mL of dioxane was degassed by bubbling N$_2$ for 5 min. The reaction mixture was sealed and heated in 100° C. oil bath for 1 h. The reaction mixture was loaded onto flash column (DCM to EA to EA/MeOH=100:2) to give 4-(3-(1-(7-chloro-1,5-naphthyridin-2-yl)azetidin-3-yl)pyrazin-2-yl)-2-fluoro-N-methylbenzamide (70 mg, 0.156 mmol, 72.4% yield) as a light yellow solid. $^1$H NMR (400 MHz, CHLOROFORM-d) δ ppm=8.65 (d, J=2.3 Hz, 1H), 8.59 (d, J=2.2 Hz, 1H), 8.52 (d, J=2.2 Hz, 1H), 8.28 (t, J=8.0 Hz, 1H), 8.05 (d, J=9.2 Hz, 1H), 8.01 (br. s., 1H), 7.47-7.32 (m, 2H), 6.88-6.81 (m, 1H), 6.80 (d, J=9.2 Hz, 1H), 4.56-4.43 (m, 4H), 4.43-4.33 (m, 1H), 3.09 (d, J=4.3 Hz, 3H). m/z=449 (M+1).

BIOLOGICAL EXAMPLES

The worldwide market for therapies for CNS disorders is worth more than $50 billion and is set to grow substantially in the years ahead. This is because: 1) the incidence of many CNS disorders (e.g., Alzheimer's disease, stroke, and Parkinson's disease) increase exponentially after age 65 and 2) the number of people in the world over 65 is about to increase sharply due to a marked rise in fertility after World War II. However, CNS research and development are associated with significant challenges: it takes longer to get a CNS drug to market (12-16 years) compared with a non-CNS drug (10-12 years) and there is a higher attrition rate for CNS drug candidates than for non-CNS drug candidates. This is attributable to a variety of factors, including the complexity of the brain, the requirement of CNS drugs to cross the blood-brain barrier (BBB), and the liability of CNS drugs to cause CNS side effects. The compounds of the invention may be modified by appending appropriate functionalities to enhance selective biological properties, such as BBB penetration, along with pharmacokinetics and drug metabolism, in the process of the discovery and development of safe and effective medicines for CNS disorders.

Surprisingly, the compounds of the present invention exhibit improved pharmacokinetics and pharmacodynamics, which relate, directly and indirectly, to the ability of the compound to be effective for its intended use. For example, the compounds have been surprisingly found to possess improved receptor occupancy (ex vivo RO) coupled with improved selectivity against PDE2A as shown in Table 1 in terms of IC$_{50}$ (μM). In addition, because the compounds of the invention also possess desirable clearance and permeability/efflux properties, they readily lend themselves to predicting in vivo PK and PD properties, which in turn assist in projection of therapeutic target coverage and efficacious dosages via in vivo absorption, distribution, metabolism and excretion properties. Increased biological penetration into a given biological compartment (e.g., blood, lymphatic system, central nervous system), increased oral availability, increased solubility, and altered clearance, metabolism and/or rate of excretion are important factors for determining which compounds may be useful drugs and which may not.

TABLE 1

| Ex. No. | PDE10A (μM) | PDE2A (μM) | Ex vivo RO $^A$10 mpk 1 h $^B$10 mpk 4 h $^C$3 mpk 4 h | Average Permeability LLC-PK1 | rat MDR1 efflux ratio in LLC-PK1 | human MDR1 efflux ratio in LLC-PK1 |
|---|---|---|---|---|---|---|
| 1 | 0.0287 | 10 | 79% +/− 7.8%$^B$ | 16.0 | 2.3 | 2.9 |
|   |        |    | 58.8% +/− 13.5%$^C$ |    |    |    |
| 2 | 0.0063 | 10 | 112% +/− 4.3%$^B$ | 28.2 | 2.7 | 2.4 |
|   |        |    | 72% +/12.4%$^C$ |    |    |    |
| 3 | 0.0031 | 10 | 97.4% +/− 10.7%$^C$ | 43.6 | 2.1 | 2 |
| 4 | 0.0028 | 10 | 93.3% +/− 10%$^C$ | 26.5 | 2.2 | 3.4 |
| 5 | 0.0075 | 10 | 68.3% +/− 15%$^C$ | 24.9 | 2.3 | 2.5 |
| 6 | 0.0076 | 10 | 85.4% +/− 22.3%$^A$ | 38.8 | 1.2 | 1.8 |
|   |        |    | 62.6% +/− 11.0%$^C$ |    |    |    |
| 7 | 0.004  | 10 | 93.2% +/− 8.6%$^A$ | 32.6 | 3.1 | 2.95 |
|   |        |    | 109.8% +/− 12.4%$^C$ |    |    |    |
| 8 | 0.0005 | 10 | 134% +/− 5.3%$^A$ | 33.1 | 2.5 | 2.8 |
|   |        |    | 83.5% ± 7.2%$^C$ |    |    |    |

TABLE 1-continued

| Ex. No. | PDE10A (μM) | PDE2A (μM) | Ex vivo RO [A]10 mpk 1 h [B]10 mpk 4 h [C]3 mpk 4 h | Average Permeability LLC-PK1 | rat MDR1 efflux ratio in LLC-PK1 | human MDR1 efflux ratio in LLC-PK1 |
|---|---|---|---|---|---|---|
| 9 | 0.0309 | 10 | 123.4% +/− 10.8%[A]<br>87.1% +/− 7.1%[B]<br>61.8% +/− 19.3%[C] | 39.7 | 2.7 | 1.8 |
| 10 | 0.0059 | 7.375 | 100.6% +/− 13.1%[A]<br>108% +/− 8.0%[C] | 39.5 | 1.2 | 1.8 |
| 11 | 0.0166 | 10 | 80% +/− 12.0%[B]<br>67.5% +/− 8.3%[C] | 44.5 | 1.2 | 1.75 |
| 12 | 0.0039 | 10 | 91.4% +/− 15.1%[C] | 37.7 | 2.8 | 1.85 |
| 13 | 0.0017 | 10 | 77% +/− 8.4%[C] | 38.0 | 2.7 | 3.025 |
| 14 | 0.0036 | 10 | 78.5% +/− 8.3%[C] | 52.1 | 1.1 | 1.25 |
| 15 | 0.0013 | 10 | 47.7% +/− 11.6%[A] | 22.7 | 3.1 | 10.4 |
| 16 | 0.0026 | 3.304 | 52.3% +/− 38.3%[A] | 49.1 | 1.2 | 1.9 |
| 17 | 0.0020 | 2.163 | 72% ± 23%[A] | 36.6 | 76 | 41 |

The above biological activity data were obtained by using the following assays of Examples A, B, F and G. Compounds 15, 16, and 17 have the following structures, respectively:

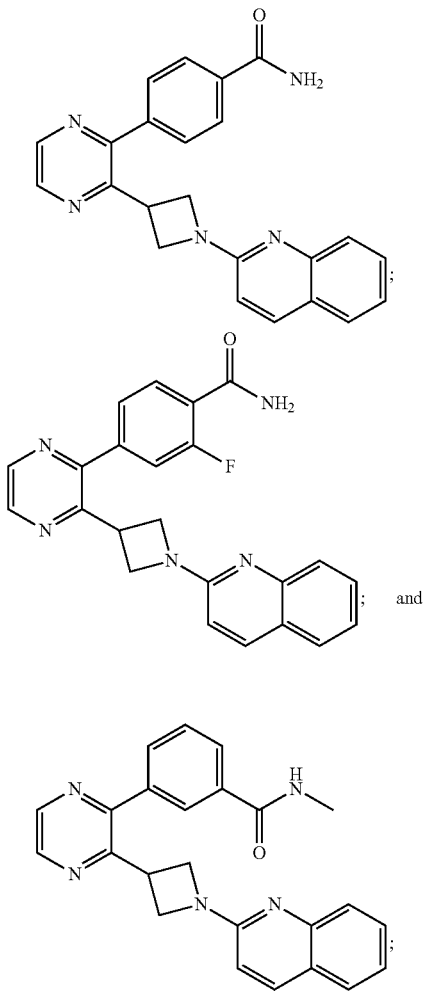

and are named: 4-(3-(1-(2-quinolinyl)-3-azetidinyl)-2-pyrazinyl)benzamide; 2-fluoro-4-(3-(1-(quinolin-2-yl)azetidin-3-yl)pyrazin-2-yl)benzamide; and N-methyl-3-(3-(1-(quinolin-2-yl)azetidin-3-yl)pyrazin-2-yl)benzamide.

Example A

PDE10A Enzyme Activity and Inhibition

Enzyme Activity

An IMAP TR-FRET assay was used to analyze the enzyme activity (Molecular Devices Corp., Sunnyvale Calif.). 10 μL of serial diluted PDE10A (BPS Bioscience, San Diego, Calif.) or tissue homogenate was incubated with equal volumes of diluted fluorescein labeled cAMP or cGMP for 90 min in 384-well Polypropylene assay plates (Greiner, Monroe, N.C.) at room temperature. After incubation, the reaction was stopped by adding 55 μL of diluted binding reagents and was incubated for 4 hours to overnight at room temperature. The plates were read on an Envision (Perkin Elmer, Waltham, Mass.) for time resolved fluorescence resonance energy transfer. The data were analyzed with Genedata Screener® (Lexington, Mass.).

Enzyme Inhibition.

To check the inhibition profile, 0.2 μL of serial diluted compounds were incubated with 10 μL of diluted PDE10 enzyme (BPS Bioscience, San Diego, Calif.) or tissue homogenate in a 384-well Polypropylene assay plate (Greiner, Monroe, N.C.) for 60 min at room temperature. After incubation, 10 μL of diluted fluorescein labeled cAMP or cGMP substrate was added and incubated for 90 min at room temperature. The reaction was stopped by adding 55 μL of diluted binding reagents and plates were read on an Envision (Perkin Elmer, Waltham, Mass.) for time resolved fluorescence resonance energy transfer. The data were analyzed with Genedata Screener® (Lexington, Mass.).

Example B

PDE IMAP Assay Protocol

Purified human PDE2A1 and PDE10A2 enzymes were obtained from BPS Bioscience (San Diego, Calif.). IMAP™ TR-FRET progressive binding system, FAM-cAMP substrate were from Molecular Devices (Sunnyvale, Calif.).

The PDE IMAP assay was conducted in a 384-well black Greiner polypropylene plate (Sigma, St. Louis, Mo.). PDE inhibitors were serial diluted in 100% DMSO and dispensed into assay plate at 200 mL per well using Echo® Liquid Handling System from LABCYTE. Ten μL of PDE enzyme in IMAP reaction buffer (10 mM Tris-HCl, pH 7.2, 10 mM $MgCl_2$, 0.05% $NaN_3$, and 0.01% Tween-20) was added into the assay wells. The PDE enzyme concentration used was based on each lot of enzyme activity, to ensure enzyme reaction falls in a linear range under assay condition. 1.4 nM of PDE2 or 8 μM PDE10 were used in the assay system. Enzyme was pre-incubated with inhibitors for 60 minutes at room temperature before addition of 10 uL of substrate addition, which results in 100 nM of FAM-cAMP in the reaction. Enzyme reaction was allowed to proceed at room temperature for 90 min, and the reaction is stopped by 55 μl addition of binding reagent according to manufacturer's recommendation. The mixture is further incubated at room temperature for additional 4 hours, and signal was read on an Envision multimode reader (PerkinElmer). Fluorescence signals were measured at 520 nm and 485 nm. The signal ratio at 520/485 nm corresponded to the generation of reaction product of AMP, and it was used in all data analysis. Values from DMSO-treated wells were normalized to POC=100, and no-enzyme wells were normalized to POC=0. $IC_{50}$ values were determined by using the Genedata Screener V9.0.1. The curve fitting algorithm used for dose response data analysis in Genedata Screener is a custom implementation of a robust curve-fitting algorithm called $R_{OUT}$ (Robust regression with outlier detection) and uses a four-parameter logistical (4 PL) Hill model.

Example C

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example D

Conditioned Avoidance Responding (CAR) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example E

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase experiment
300 sec/interval (5 min)
12 intervals (1 h)
Individual on screen switches.
Start recording after first beam break.
End session after end of interval.
Cage Preparation:
Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
Animal Preparation:
Mark rats and record their weights. Bring rats to testing room.
Phase I: Habituation
Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g ½ needle or oral gavage needle) with Amgen compound solution (5 mL/kg) or risperidone (1 mL syringe with 23 g ½ needle) control (1 mL/kg) s.c.
Phase II: Compound Pre-Treatment
Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.
During phase II, prepare pcp: Dissolve pcp in saline to a concentration of 5 mg/mL.
Fill syringes (1 mL syringes with 26 g ⅜ needle) with pcp solution (1 mL/kg).
Phase III: PCP Administration.
Make sure phase II is ended. Remove rat from enclosure, start the next phase using on-screen individual switch, administer pcp s.c. and place rat back in the enclosure. The computer will record for 1 h.
Clean-Up:
End-session to terminate experiment and so that computer will compile data. Export raw data to spreadsheet file for data analysis. Euthanize rats and take necessary tissue/sample for PK.
Data Generation:
Export raw data to spreadsheet file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

Example F

PDE10 Ex Vivo Receptopr Occupancy (RO) Screening Protocol

The ex vivo screening protocol was approved by Amgen's Institutional Animal Care and Use Committee (IACUC) and in accordance with the National Institutes of Health Guide for Care and Use of Laboratory Animals in facilities accredited by the Association for the Assessment and Accreditation of Laboratory Animal Care (AALAC).
PDE10 inhibitors were dissolved in 2% Hydroxypropylmethylcellulose (HPMC), 1% Tween-80, pH 2.2 with methanesulfonic acid. Male Sprague Dawley® rats weighing 180-225 g (4 per group) were dosed orally with either vehicle or PDE10 inhibitors (3 mg/kg or 10 mg/kg) and then returned to their home cage to allow for absorption of the compounds. After one hour (with 10 mg/kg PDE10 inhibitor) or four hours (with 3 mg/kg or 10 mg/kg PDE10 inhibitor) rats were sacrificed by $CO_2$ inhalation. Blood was obtained by heart puncture and plasma was frozen and stored at −80° C. for exposure analysis. Brains were removed and immediately frozen in chilled methylbutane, and stored at −80° C. until cutting. Three coronal brain slices per brain containing the striatum were cut at 20 mm using a cryostat and placed onto microscope slides, air-dried and stored at −20° C. For radioligand binding experiments, slides were thawed at room temperature and then incubated with 1 nM a tritium labeled tracer compound (insert citation) in binding buffer (150 mM Phosphate-buffered saline containing 2 mM $MgCl_2$ and 100 mM DTT, pH 7.4) for 1 minute at 4° C. To assess non-specific binding, slides containing adjacent brain sections were incubated in the same solution with addition of 10 mM of an unlabelled, structurally unrelated PDE10 antagonist. Afterwards slides were washed 3 times in ice-cold binding buffer, dipped into distilled water to remove buffer salts, and dried under a stream of cold air. Emission of beta particles from the sections was counted for 8 hours in a Beta Imager 2000 (Biospace, Paris, France) and digitized and analyzed using M3 Vision software (Biospace, Paris, France). Total binding radioactivity in the striatum was measured as $cpm/mm^2$ in hand-drawn regions of interest and averaged across the three sections per brain. Non-specific binding was subtracted to obtain specific binding values and percent occupancy was calculated by setting vehicle specific binding as 0% occupancy.

Example G

Permeability and Transcellular Transport Protocol

Materials
Digoxin and mannitol were purchased from Sigma-Aldrich (St. Louis, Mo.). 3H-digoxin and 14C-mannitol were purchased from PerkinElmer Life and Analytical Sciences (Boston, Mass.). Transport buffer was prepared using Hank's balanced salt solution (HBSS) supplemented with 10 mM Hepes, pH 7.4 and 0.1% BSA (HHBSS, Invitrogen, Grand Island, N.Y., BSA, Bovine Serum Albumin, Calbiochem, La Jolla, Calif.).
Cell Lines and Cell Cultures.
Cultures were incubated at 37° C. in a humidified (95% relative humidity) atmosphere of 5% $CO_2$/95% air. The parental cell line LLC-PK1 (porcine renal epithelial cells) was purchased from American Type Culture Collection (ATCC, Manassas, Va.). Human MDR1 and Sprague-Dawley rat mdra1 transfectants in LLC-PK1 were generated at Amgen (Thousand Oaks, Calif.). Cells were cultured in Medium 199 supplemented with 2 mM L-glutamine, penicillin (50 units/mL), streptomycin (50 μg/mL), and 10% (v/v) fetal bovine serum (all from Invitrogen) (Schinkel et al, 1995).
Permeability and Transcellular Transport of Test Compounds
LLC-PK1, MDR1-LLC-PK1, and mdr1a-LLC-PK1 cell monolayers were seeded onto porous (1.0 μm) polycarbonate 96-well transwell membrane filters (Millipore Corp., Billerica, Mass.) and cultured for six days with one media replacement on day four prior to transwell experiments. Cells were washed once with warmed HHBS prior to transwell experiments. Experiments were initiated by replacing the buffer in each compartment with 0.15 mL of HBSS containing 0.1% BSA with and without 5 μM of test compound in triplicate wells. The plates were incubated for two hours at 37° C. in an EVO incubator with shaking. Aliquots (100 μl) from both donor and receiver chambers were transferred to 96 well plates or scintillation vials. Protein was precipitated by addition of 200 μL acetonitrile containing 0.1% formic acid and prazosin (25 ng/mL) as internal standard. After vortexing and centrifugation at 3000 rpm for 20 min, 150 μL supernatant samples were transferred to a new plate containing 50 μL water for LC-MS/MS analysis. Transcellular transport of 3H-Digoxin was used as a positive control for Pgp. Paracellular permeability of 14C-Mannitol was used to measure the integrity of the monolayer. Sample radioactivity was measured using a liquid scintillation counter (Packard Tri-Carb 2910TR, PerkinElmer).
The apparent permeability coefficient (Papp) of all tested agents was estimated from the slope of cumulative amount (dQ) of the agent vs. time (dt), and the equation:

$$Papp=(dQ/dt)/(A*C0)$$

where dQ/dt is the penetration rate of the agent (μm/s), A is the surface area of the cell layer on the Transwell (0.11 cm2), and C0 is the initial concentration of the test compound (μM).
The foregoing is merely illustrative of the invention and is not intended to limit the invention to the disclosed compounds. Variations and changes which are obvious to one skilled in the art are intended to be within the scope and nature of the invention which are defined in the appended claims. All patents, patent applications, and other publications recited herein are hereby incorporated by reference in their entirety.

What is claimed is:
1. A compound, which is:

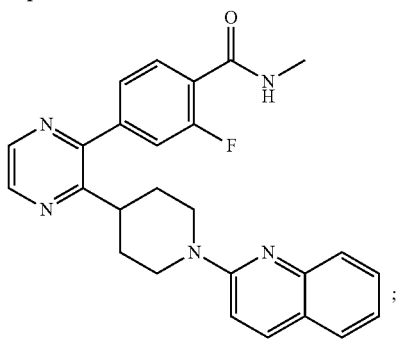

or a pharmaceutically acceptable salt thereof.
2. A compound, which is:

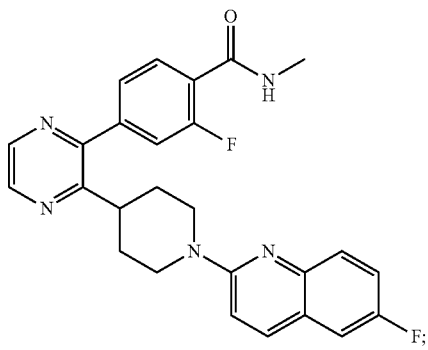 [SMILES: CNC(=O)c1ccc(-c2nccnc2C2CCN(c3ccc4cc(F)ccc4n3)CC2)cc1F]

or a pharmaceutically acceptable salt thereof.
3. A compound, which is:

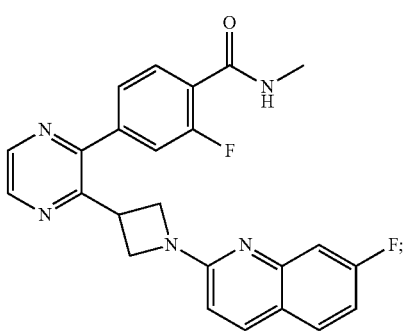 [SMILES: CNC(=O)c1ccc(-c2nccnc2C2CN(c3ccc4ccc(F)cc4n3)C2)cc1F]

or a pharmaceutically acceptable salt thereof.
4. A compound, which is:

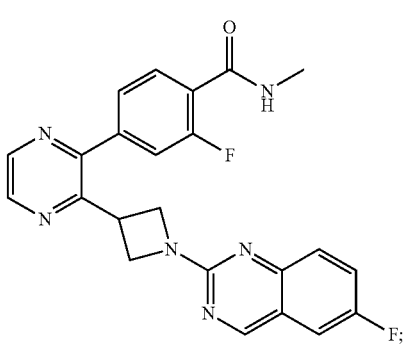 [SMILES: CNC(=O)c1ccc(-c2nccnc2C2CN(c3ncc4cc(F)ccc4n3)C2)cc1F]

or a pharmaceutically acceptable salt thereof.

5. A compound, which is:

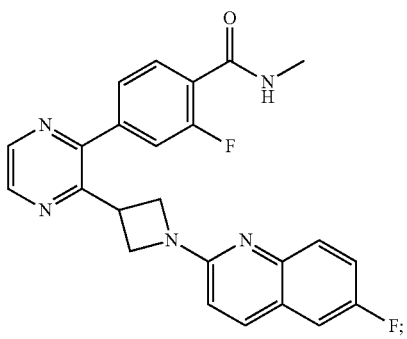 [SMILES: CNC(=O)c1ccc(-c2nccnc2C2CN(c3ccc4cc(F)ccc4n3)C2)cc1F]

or a pharmaceutically acceptable salt thereof.
6. A compound, which is:

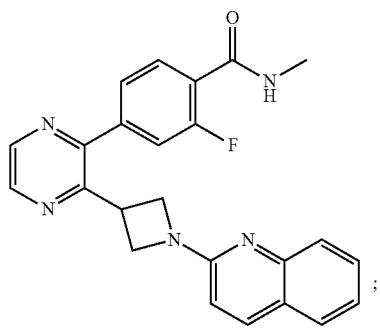 [SMILES: CNC(=O)c1ccc(-c2nccnc2C2CN(c3ccc4ccccc4n3)C2)cc1F]

or a pharmaceutically acceptable salt thereof.
7. A compound, which is:

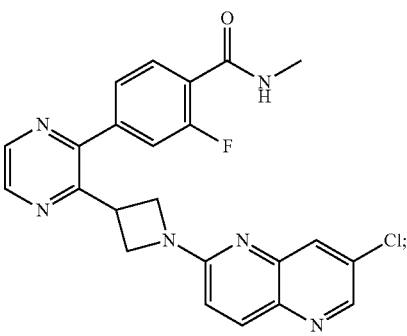 [SMILES: CNC(=O)c1ccc(-c2nccnc2C2CN(c3ccc4ncc(Cl)cc4n3)C2)cc1F]

or a pharmaceutically acceptable salt thereof.
8. A pharmaceutical composition comprising a compound according to any one of claims 1-7, or a pharmaceutically acceptable salt thereof, and a pharmaceutically acceptable excipient.

* * * * *